US011432590B2

(12) United States Patent
Yamada et al.

(10) Patent No.: US 11,432,590 B2
(45) Date of Patent: Sep. 6, 2022

(54) INHALATION COMPONENT GENERATION DEVICE, METHOD FOR CONTROLLING INHALATION COMPONENT GENERATION DEVICE, AND PROGRAM

(71) Applicant: JAPAN TOBACCO INC., Tokyo (JP)

(72) Inventors: Manabu Yamada, Tokyo (JP); Manabu Takeuchi, Tokyo (JP); Takeshi Akao, Tokyo (JP); Takuma Nakano, Tokyo (JP); Hajime Fujita, Tokyo (JP)

(73) Assignee: JAPAN TOBACCO INC., Tokyo (JP)

( * ) Notice: Subject to any disclaimer, the term of this patent is extended or adjusted under 35 U.S.C. 154(b) by 197 days.

(21) Appl. No.: 16/856,073

(22) Filed: Apr. 23, 2020

(65) Prior Publication Data
US 2020/0245690 A1  Aug. 6, 2020

Related U.S. Application Data

(63) Continuation of application No. PCT/JP2017/038224, filed on Oct. 23, 2017.

(51) Int. Cl.
*A24F 40/50* (2020.01)
*A24F 40/60* (2020.01)
(Continued)

(52) U.S. Cl.
CPC ............. *A24F 40/53* (2020.01); *A24F 40/50* (2020.01); *A24F 40/60* (2020.01); *A24F 40/90* (2020.01);
(Continued)

(58) Field of Classification Search
CPC .......... A24F 40/53; A24F 40/90; A24F 40/50; A24F 40/60; G01N 21/3504; A61M 15/06; G01R 19/165; G01R 31/36
(Continued)

(56) References Cited

U.S. PATENT DOCUMENTS

2008/0067979 A1* 3/2008 Hayasaki .............. H01M 10/44
320/136
2009/0230117 A1* 9/2009 Fernando ................ A24F 40/50
219/490
(Continued)

FOREIGN PATENT DOCUMENTS

CN   105611847 A   5/2016
CN   106255428 A   12/2016
(Continued)

OTHER PUBLICATIONS

Chinese Office Action dated Dec. 1, 2020, in corresponding Chinese Patent Application No. 201780096214.5.
(Continued)

*Primary Examiner* — Jeffrey P Aiello
(74) *Attorney, Agent, or Firm* — Xsensus LLP

(57) ABSTRACT

An inhalation component generation device including: a load configured to vaporize or atomize an inhalation component source by electric power from an electric power source; a user interface; and circuitry configured to obtain a value representing a remaining amount of the electric power source, obtain an operation requesting signal to the load, and generate an instruction for operating the load; cause the user interface to perform a first notification in a case that the value is equal to or greater than a first threshold value; cause the user interface to perform a second notification in a case that the value is less than the first threshold value and equal to or greater than a second threshold value that is less than the first threshold value; and cause the user interface to perform a third notification in a case that the value is less than the second threshold value.

19 Claims, 19 Drawing Sheets

(51) Int. Cl.
    *A24F 40/90*     (2020.01)
    *A24F 40/53*     (2020.01)
    *G01N 21/3504*     (2014.01)
    *A24F 40/40*     (2020.01)
    *A24F 40/10*     (2020.01)

(52) U.S. Cl.
    CPC .......... *G01N 21/3504* (2013.01); *A24F 40/10* (2020.01); *A24F 40/40* (2020.01)

(58) Field of Classification Search
    USPC ................................ 702/1, 63, 85, 108, 137
    See application file for complete search history.

(56) References Cited

U.S. PATENT DOCUMENTS

| | | | | |
|---|---|---|---|---|
| 2012/0296587 | A1* | 11/2012 | Sugiyama | G01R 31/367 702/63 |
| 2013/0019887 | A1* | 1/2013 | Liu | A24F 40/40 131/329 |
| 2013/0042865 | A1* | 2/2013 | Monsees | A24F 1/32 128/203.27 |
| 2014/0053856 | A1* | 2/2014 | Liu | A24F 40/60 131/329 |
| 2015/0027223 | A1* | 1/2015 | Kishimoto | H01B 1/02 73/305 |
| 2015/0216233 | A1* | 8/2015 | Sears | A24F 40/40 362/230 |
| 2015/0272223 | A1* | 10/2015 | Weigensberg | G08B 7/06 131/328 |
| 2016/0205998 | A1* | 7/2016 | Matsumoto | A24F 40/20 |
| 2017/0047756 | A1* | 2/2017 | Xiang | H02J 7/0045 |
| 2017/0258135 | A1* | 9/2017 | Yerkic-Husejnovic | H02J 7/0045 |
| 2017/0258136 | A1* | 9/2017 | Hawes | A24F 40/65 |

FOREIGN PATENT DOCUMENTS

| | | |
|---|---|---|
| CN | 106714288 A | 5/2017 |
| JP | 08-191502 A | 7/1996 |
| JP | 11-103334 A | 4/1999 |
| JP | 2008-072870 A | 3/2008 |
| JP | 2010-104310 A | 5/2010 |
| JP | 2011-53097 A | 3/2011 |
| JP | 2011-515080 A | 5/2011 |
| JP | 2014-524313 A | 9/2014 |
| JP | 2017-511690 A | 4/2017 |
| WO | 2014/150942 A2 | 9/2014 |
| WO | 2015/046386 A1 | 4/2015 |
| WO | 2015/052513 A2 | 4/2015 |
| WO | 2015/073975 A1 | 5/2015 |
| WO | 2015/119918 A1 | 8/2015 |
| WO | 2015/155612 A2 | 10/2015 |
| WO | 2015/161502 A1 | 10/2015 |
| WO | 2015/165747 A1 | 11/2015 |

OTHER PUBLICATIONS

International Search Report and Written Opinion dated Nov. 28, 2017 for PCT/JP2017/038224 filed on Oct. 23, 2017, 14 pages including English Translation of the International Search Report.
International Search Report and Written Opinion dated Nov. 28, 2017 for PCT/JP2017/038222 filed on Oct. 23, 2017, 14 pages including English Translation of the International Search Report.
International Search Report and Written Opinion dated Nov. 28, 2017 for PCT/JP2017/038223 filed on Oct. 23, 2017, 6 pages including English Translation of the International Search Report.
International Preliminary Report on Patentability and Written Opinion of the International Searching Authority dated Nov. 28, 2017 in International Application No. PCT/JP2017/038222, 9 pages. (Previously filed; submitting English translation only.).
Taiwanese Examiner Interview Summary dated Feb. 20, 2021, in corresponding Taiwanese Patent Application No. 106137923.
Extended European Search Report dated Jun. 11, 2021, in corresponding European Patent Application No. 17929643.9.
U.S. Office Action dated Jun. 3, 2021, in corresponding U.S. Appl. No. 16/856,260.
Office Action dated May 28, 2021, in corresponding Canadian patent Application No. 3079379, 6 pages.

\* cited by examiner

INHALATION COMPONENT GENERATION DEVICE, METHOD FOR CONTROLLING INHALATION COMPONENT GENERATION DEVICE, AND PROGRAM

CROSS REFERENCE TO RELATED APPLICATIONS

The present application is a continuation application of International Application No. PCT/JP2017/038224, filed on Oct. 23, 2017.

TECHNICAL FIELD

The present invention relates to an inhalation component generation device which comprises a load that vaporizes or atomizes an inhalation component source by electric power from an electric power source.

BACKGROUND ART

In place of a cigarette, an inhalation component generation device (an electronic cigarette) for tasting an inhalation component, that is generated by vaporizing or atomizing a flavor source such as tobacco and so on and an aerosol source by a load such as a heater, has been suggested (Patent Literatures 1-8). The inhalation component generation device comprises a load for vaporizing or atomizing a flavor source and/or an aerosol source, an electric power source for supplying electric power to the load, and a control unit for controlling the load and the electric power source.

Patent Literatures 2-7 disclose inhalation component generation devices which comprise an LED(s) (Light Emitting Diode). Especially, Patent Literatures 4-7 disclose that the number of LEDs, that are installed in the device, to be turned on is changed, or the lighting pattern of an LED(s) is changed, in response to a state of charge of an electric power source.

Also, Patent Literature 9 discloses setting a management voltage value corresponding to degradation information relating to an electric power source, before the voltage of the electric power source reaches a discharge cutoff voltage. A control unit performs processing for terminating discharge of a secondary battery, when the voltage of the electric power source becomes a value equal to or less than the management voltage value.

CITATION LIST

Patent Literature

PTL 1: PCT international publication No. WO 2015/165747
PTL 2: United States Patent Application Publication No. US 2013/0019887
PTL 3: PCT international publication No. WO 2015/046386
PTL 4: PCT international publication No. WO 2015/073975
PTL 5: United States Patent Application Publication No. US 2015/0272223
PTL 6: PCT international publication No. WO 2015/119918
PTL 7: PCT international publication No. WO 2015/161502
PTL 8: PCT international publication No. WO 2014/150942
PTL 9: Japanese Patent Application Public Disclosure No. 2011-53097

SUMMARY OF INVENTION

The gist of a first characteristic is that the first characteristic comprises an inhalation component generation device which comprises a load that vaporizes or atomizes an inhalation component source by electric power from an electric power source, a notification unit, and a control unit that obtains a value representing a remaining amount of the electric power source, and obtains an operation requesting signal to the load and generates an instruction for operating the load; wherein the control unit is configured to cause the notification unit to perform a first notification when the value representing the remaining amount of the electric power source is equal to or greater than a first threshold value; the control unit is configured to cause the notification unit to perform a second notification when the value representing the remaining amount of the electric power source is less than the first threshold value and equal to or greater than a second threshold value that is less than the first threshold value; the control unit is configured to cause the notification unit to perform a third notification when the value representing the remaining amount of the electric power source is less than the second threshold value; and the first notification, the second notification and the third notification are different from each other.

The gist of a second characteristic is that the second characteristic comprises the inhalation component generation device in the first characteristic, wherein the notification unit comprises a light emitting element, the first notification comprises a first light emission color by the light emitting element, the second notification comprises a second light emission color by the light emitting element, the third notification comprises a third light emission color by the light emitting element, and the first light emission color, the second light emission color and the third light emission color are different from each other.

The gist of a third characteristic is that the third characteristic comprises the inhalation component generation device in the second characteristic, wherein the first light emission color includes a cold color, the third light emission color includes a warm color, and the second light emission color includes an intermediate color that is between the first light emission color and third light emission color in a hue circle.

The gist of a fourth characteristic is that the fourth characteristic comprises the inhalation component generation device in the second characteristic or the third characteristic, wherein the distance between a complementary color of the first light emission color and the third light emission color on the hue circle is shorter than the distance between the complementary color of the first light emission color and the second light emission color on the hue circle.

The gist of a fifth characteristic is that the fifth characteristic comprises the inhalation component generation device in any one of the second characteristic to the fourth characteristic, wherein the distance between a complementary color of the third light emission color and the first light emission color on the hue circle is shorter than the distance between the complementary color of the third light emission color and the second light emission color on the hue circle.

The gist of a sixth characteristic is that the sixth characteristic comprises the inhalation component generation device in the second characteristic, wherein a wavelength corresponding to the second light emission color is closer to a wavelength corresponding to the first light emission color than a wavelength corresponding to the third light emission color.

The gist of a seventh characteristic is that the seventh characteristic comprises the inhalation component generation device in any one of the second characteristic to the sixth characteristic, wherein the inhalation component generation device comprises one end having an inhalation port for inhaling the inhalation component and the other end opposite to the inhalation port, and the light emitting element is arranged across the other end and a part of a side face extending between the one end and the other end.

The gist of an eighth characteristic is that the eighth characteristic comprises the inhalation component generation device in the seventh characteristic, wherein the length from the one end to the other end is equal to or greater than 58 mm and equal to or less than 135 mm.

The gist of a ninth characteristic is that the ninth characteristic comprises the inhalation component generation device in the eighth characteristic, wherein the length from the one end to the other end is equal to or greater than 100 mm and equal to or less than 135 mm.

The gist of a tenth characteristic is that the tenth characteristic comprises the inhalation component generation device in any one of the second characteristic to the sixth characteristic wherein the inhalation component generation device comprises one end having an inhalation port for inhaling the inhalation component and the other end opposite to the inhalation port, and the light emitting element is arranged at a side face which extends between the one end and the other end.

The gist of an eleventh characteristic is that the eleventh characteristic comprises the inhalation component generation device in any one of the second characteristic to the tenth characteristic, wherein the load can generate the inhalation component from the inhalation component source when the value representing the remaining amount of the electric power source is equal to or greater than the second threshold value, and the light emitting pattern of the light emitting element for the first notification is the same as that for the second notification.

The gist of a twelfth characteristic is that the twelfth characteristic comprises the inhalation component generation device in any one of the first characteristic to the eleventh characteristic, wherein the load can generate the inhalation component from the inhalation component source, when the value representing the remaining amount of the electric power source is equal to or greater than the second threshold value; and the control unit controls the periods of the first notification and the second notification performed by the notification unit to vary, according to the period that the operation requesting signal is continuously obtained.

The gist of a thirteenth characteristic is that the thirteenth characteristic comprises the inhalation component generation device in any one of the first characteristic to the twelfth characteristic, wherein the load can generate the inhalation component from the inhalation component source, when the value representing the remaining amount of the electric power source is equal to or greater than the second threshold value; and at least one of the notification timing and the notification period of the first notification, when the operation requesting signal is detected, is the same as that of the second notification.

The gist of a fourteenth characteristic is that the fourteenth characteristic comprises the inhalation component generation device in any one of the first characteristic to the thirteenth characteristic, wherein the control unit controls the notification unit to perform the third notification for a predetermined period that is independent of the period that the operation requesting signal is continuously obtained.

The gist of a fifteenth characteristic is that the fifteenth characteristic comprises the inhalation component generation device in the fourteenth characteristic, wherein the period that each of the first notification and the second notification is performed by the notification unit is shorter than the predetermined period.

The gist of a sixteenth characteristic is that the sixteenth characteristic comprises the inhalation component generation device in any one of the first characteristic to the fifteenth characteristic, wherein the first threshold value is a variable value.

The gist of a seventeenth characteristic is that the seventeenth characteristic comprises an inhalation component generation device comprising a load that vaporizes or atomizes an inhalation component source by electric power from an electric power source, a notification unit, and a control unit that obtains an operation requesting signal to the load and generates an instruction for operating the load, and is able to control the notification unit to operate in one of a normal use mode, a charge requesting mode and an abnormality notifying mode; wherein notifications performed by the notification unit in the normal use mode, the charge requesting mode and the abnormality notifying mode are different from each other.

The gist of an eighteenth characteristic is that the eighteenth characteristic comprises a method for controlling an inhalation component generation device comprising a load that vaporizes or atomizes an inhalation component source by electric power from an electric power source, and the method comprises: obtaining a value representing a remaining amount of the electric power source; obtaining an operation requesting signal to the load and generating an instruction for operating the load; performing a first notification when the value representing the remaining amount of the electric power source, that is obtained in the obtaining of the value, is equal to or greater than a first threshold value; performing a second notification when the value representing the remaining amount of the electric power source, that is obtained in the obtaining of the value, is less than the first threshold value and equal to or greater than a second threshold value that is less than the first threshold value; and performing a third notification when the value representing the remaining amount of the electric power source, that is obtained in the obtaining of the value, is less than the second threshold value; wherein the first notification, the second notification and the third notification are different from each other.

The gist of a nineteenth characteristic is that the nineteenth characteristic comprises a method for controlling an inhalation component generation device comprising a load that vaporizes or atomizes an inhalation component source by electric power from an electric power source, and the method comprises: obtaining an operation requesting signal to the load and generating an instruction for operating the load; and notifying one of a normal use mode, a charge requesting mode and an abnormality notifying mode; wherein notifications performed by the notification unit in the normal use mode, the charge requesting mode and the abnormality notifying mode are different from each other.

The gist of a twentieth characteristic is that the twentieth characteristic comprises a program that causes an inhalation component generation device to perform the method in the eighteenth characteristic or the nineteenth characteristic.

DESCRIPTION OF EMBODIMENTS

Figure 1:
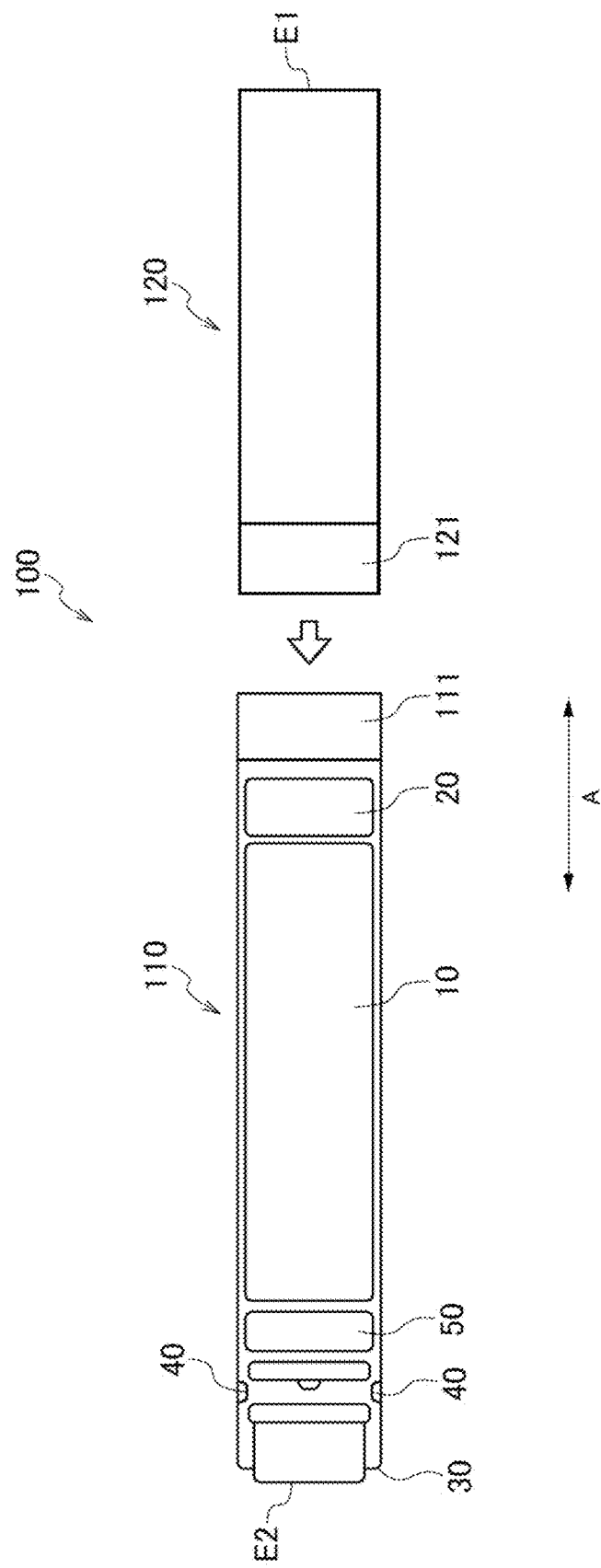
FIG. 1 is a schematic diagram of an inhalation component generation device according to an embodiment.

In the following description, embodiments will be explained. In this regard, in the following descriptions of the figures, the same or similar symbols are assigned to the same or similar parts. It should be reminded that the figures are drawn in a schematic manner, so that ratios between respective sizes and so on may be different from actual ratios and so on.

Thus, specific sizes and so on should be judged by taking the following description into consideration. Further, it is a matter of course that, in the figures, relationship and ratios between sizes in one figure may be different from those in other figures.

SUMMARY OF DISCLOSURE

Patent Literature 7 discloses a construction for changing the lighting pattern of an LED when a secondary battery is exhausted. However, in an inhalation component generation device such as, for example, an electronic cigarette, an unnatural feel sensed by a user becomes larger, if the device is made to be unusable suddenly as a result that an electric power source is exhausted. Especially, in a portable inhalation component generation device, the case that an electric power source of the device cannot be charged may occur, if the electric power source is exhausted suddenly when a charger is not carried.

According to an embodiment, an inhalation component generation device comprises a load for vaporizing or atomizing an inhalation component source by electric power from an electric power source, a notification unit, and a control unit for obtaining a value representing a remaining amount of the electric power source, and obtaining an operation requesting signal to the load and generating an instruction for operating the load. The control unit is configured to cause the notification unit to perform a first notification when the value representing the remaining amount of the electric power source is equal to or grater than a first threshold value. Also, the control unit is configured to cause the notification unit to perform a second notification when the value representing the remaining amount of the electric power source is less than the first threshold value and equal to or grater than a second threshold value that is less than the first threshold value. The control unit is configured to cause the notification unit to perform a third notification when the value representing the remaining amount of the electric power source is less than the second threshold value. The first notification, the second notification, and the third notification are different from each other.

According to the above embodiment, the notification unit can notify of the first notification, the second notification, and the third notification in response to the remaining amount of the electric power source. That is, it becomes possible to inform, by use of the second notification before performing the third notification that informs that the remaining amount of the electric power source is the minimum amount, that the remaining amount of the electric power source has been decreased. Thus, it becomes possible to give a notification to a user to request that the electric power source be charged before the remaining amount of the electric power source is exhausted.

According to another embodiment, an inhalation component generation device comprises a load for vaporizing or atomizing an inhalation component source by electric power from an electric power source, a notification unit, and a control unit which obtains an operation requesting signal to the load and generates an instruction for operating the load, and is able to control the notification unit to operate in one of a normal use mode, a charge requesting mode, and an abnormality notifying mode. Notifications performed by the notification unit in the normal use mode, the charge requesting mode, and the abnormality notifying mode are different from each other.

According to the above embodiment, the notification unit can inform a user of differences between the normal use mode, the charge requesting mode, and the abnormality notifying mode, by use of the notifications that are different from each other. Thus, in an inhalation component generation device such as an electronic cigarette wherein restriction relating to a user interface (U/I) and line off (L/O) is especially strict, the above three modes, that should be identified, can be made to be recognized by a user effectively.

First Embodiment (An inhalation component generation device)

Figure 2:
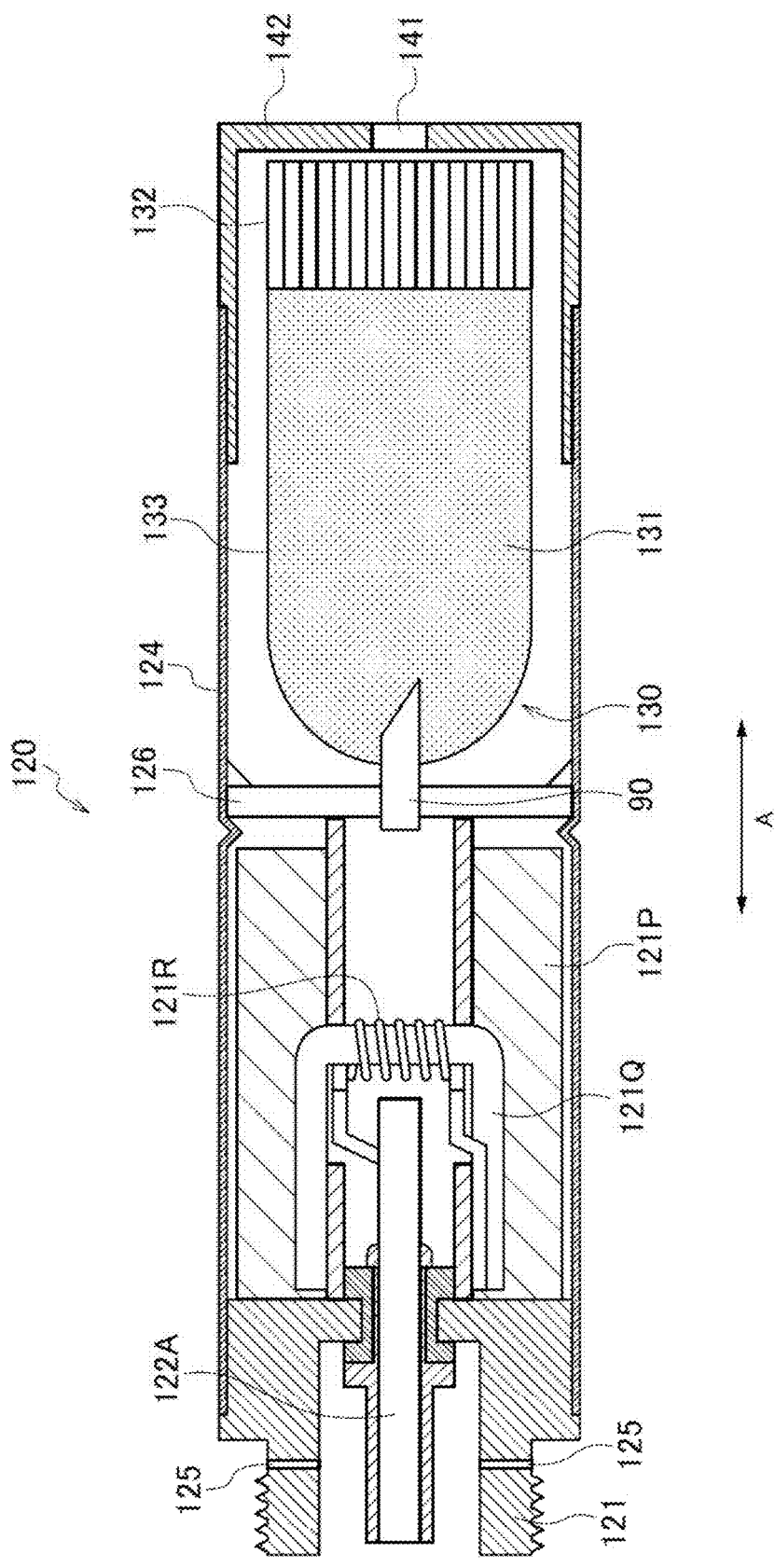
FIG. 2 is a schematic diagram of an atomizing unit according to an embodiment.
Figure 3:
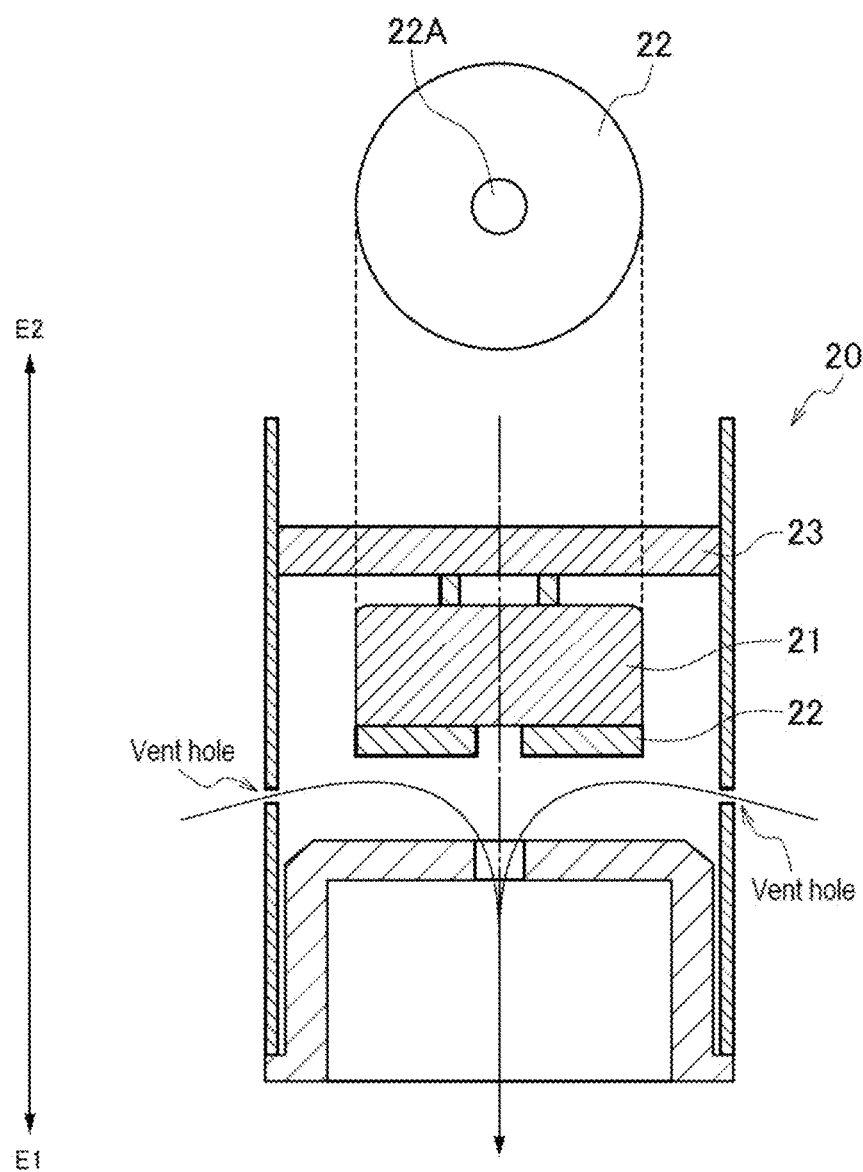
FIG. 3 is a schematic diagram of an example construction of an inhalation sensor according to an embodiment.
Figure 4:
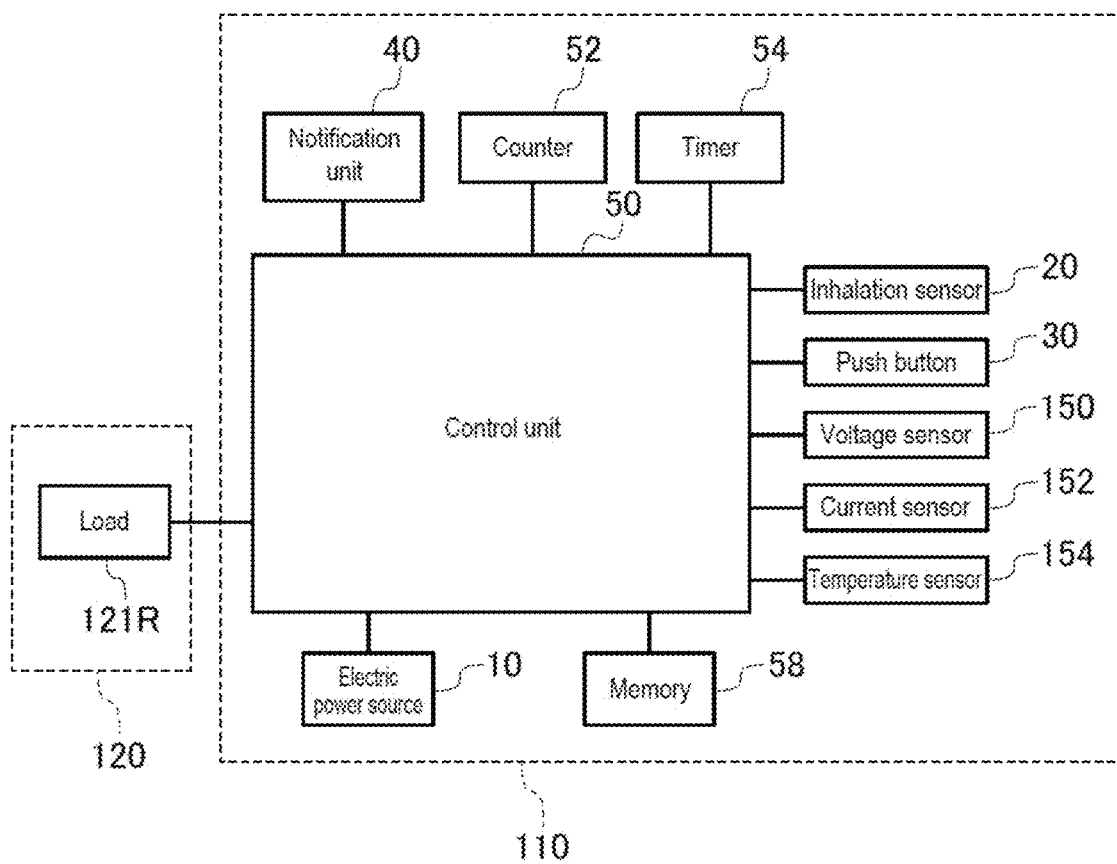
FIG. 4 is a block diagram of an inhalation component generation device.
Figure 5:
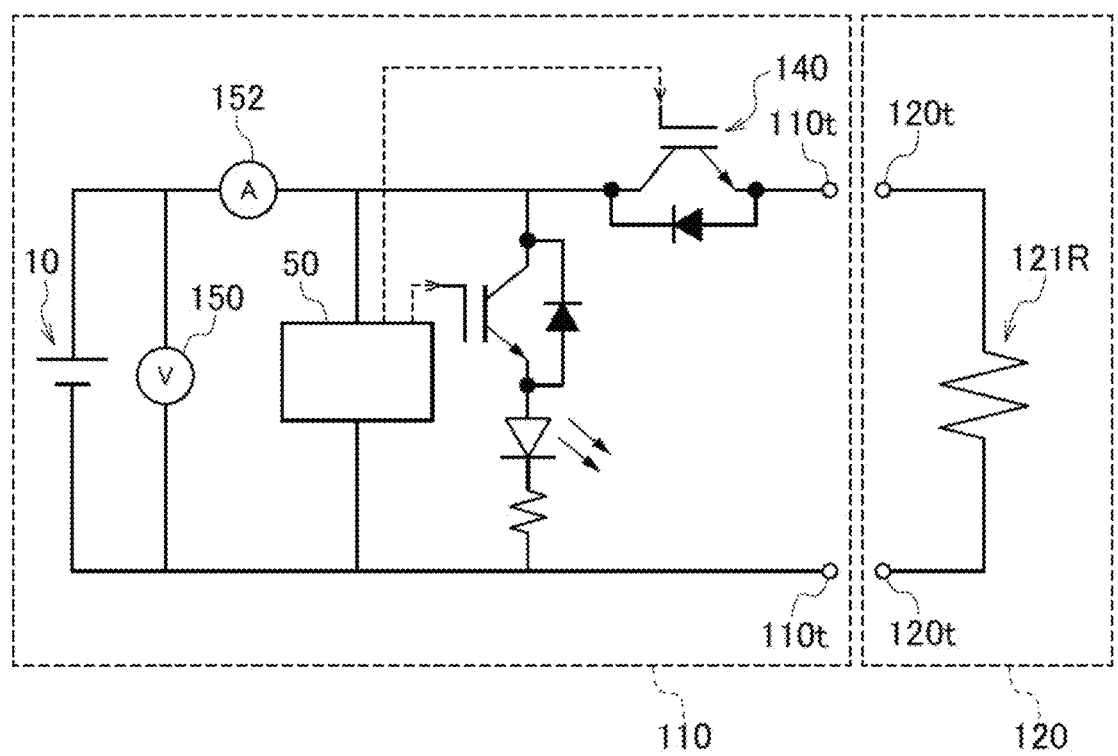
FIG. 5 is a figure showing an electric circuit of an electric equipment unit and an atomizing unit in a state that a load is being connected thereto.
Figure 6:
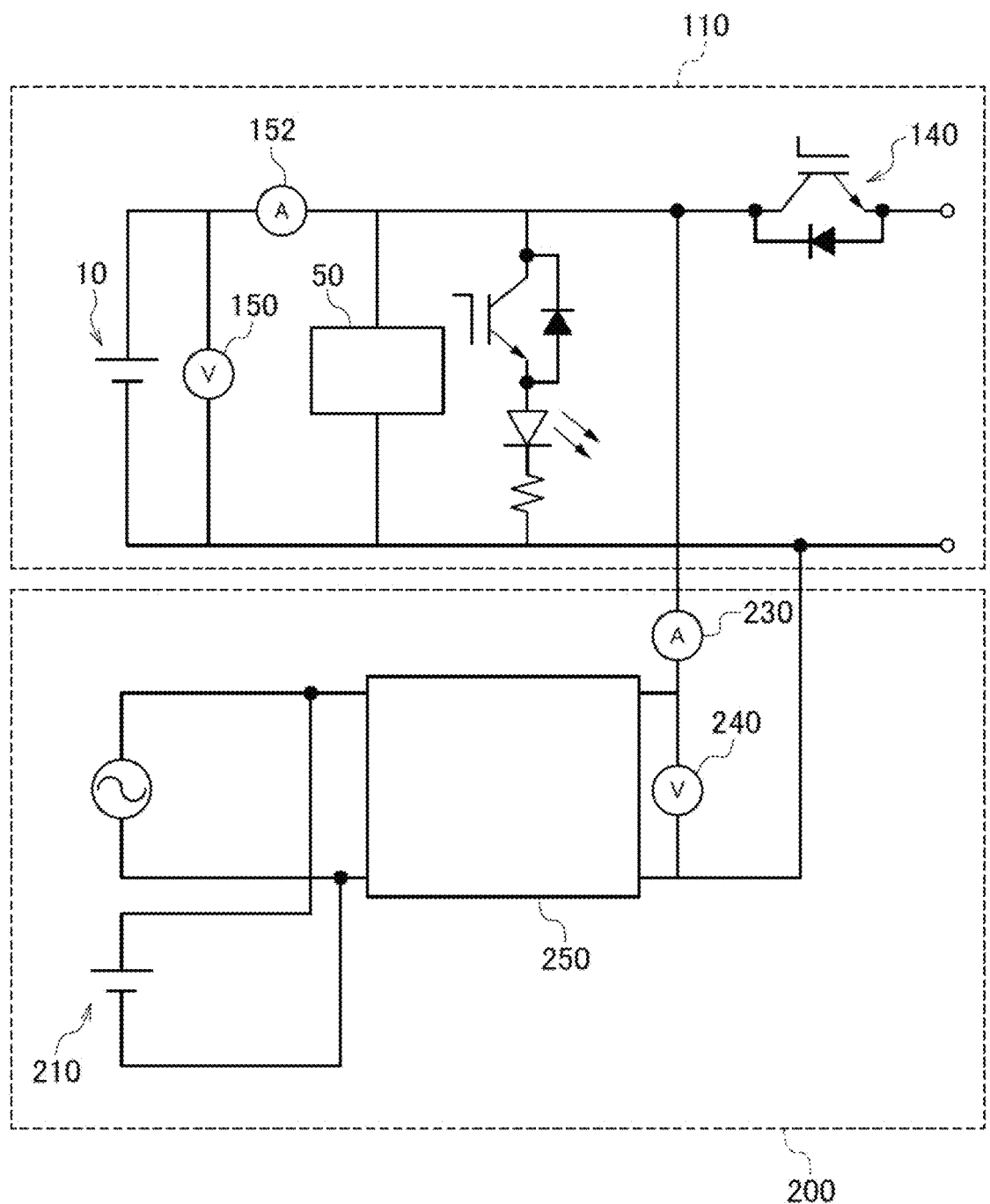
FIG. 6 is a figure showing an electric circuit of an electric equipment unit and a charger in a state that the charger is being connected.

In the following description, an inhalation component generation device according to a first embodiment will be explained. FIG. 1 is an exploded view showing an inhalation component generation device according to an embodiment. FIG. 2 is a figure showing an atomizing unit according to an embodiment. FIG. 3 is a schematic diagram showing an example embodiment of an inhalation sensor according to an embodiment. FIG. 4 is a block diagram of an inhalation component generation device. FIG. 5 is a figure showing an electric circuit of an electric equipment unit and an atomizing unit in a state that a load is connected thereto. FIG. 6 is a figure showing an electric circuit of an electric equipment unit and a charger in a state that the charger is connected.

The inhalation component generation device 100 may be a non-burning-type flavor inhaler for inhaling an inhalation component (a fragrance-inhaling-taste component) without a burning process. The inhalation component generation device 100 may have a shape that extends in a predetermined direction A that is a direction toward an inhalation end E1 from a non-inhalation end E2. In the above case, the inhalation component generation device 100 may comprise one end E1 having an inhalation port (suction opening) 141 for inhaling an inhalation component, and the other end E2 positioned opposite to the inhalation port.

The inhalation component generation device 100 may comprise an electric equipment unit 110 and an atomizing unit 120. The atomizing unit 120 is configured to be detachable/attachable from/to the electric equipment unit 110 via mechanical connection parts 111 and 112. When the atomizing unit 120 and the electric equipment unit 110 are mechanically connected to each other, a load 121R, which will be explained later, in the atomizing unit 120 is connected, via electric connection terminals 110t and 120t, to an electric power source 10 installed in the electric equipment unit 110. That is, the electric connection terminals 110t and 120t construct a connection part which can electrically connect/disconnect the load 121R to/from the electric power source 10.

The atomizing unit 120 comprises an inhalation component source that is to be inhaled by a user, and the load 121R which vaporizes or atomizes the inhalation component source by electric power from the electric power source 10. The inhalation component source may comprise an aerosol source which generates aerosol and/or a flavor source which generates a flavor component.

The load 121R may be an element which can generate aerosol and/or a flavor component from an aerosol source and/or a flavor source by receiving electric power. For example, the load 121R may be a heater element such as a heater, or an element such as an ultrasonic generator. Examples of the heater elements that can be listed are a heating resistor, a ceramic heater, an induction-heating-type heater, and so on.

In the following description, a more detailed example of the atomizing unit 120 will be explained with reference to FIG. 1 and FIG. 2. The atomizing unit 120 may comprise a reservoir 121P, a wick 121Q, and the load 121R. The reservoir 121P may be configured to store an aerosol source or a flavor source in a liquid form. For example, reservoir 121P may be a porous body constructed by use of material such as a resin web or the like. The wick 121Q may be a liquid holding member for drawing the aerosol source or the flavor source from the reservoir 121P by using a capillary phenomenon. For example, the wick 121Q may be constructed by use of a glass fiber, a porous ceramic, or the like.

The load 121R atomizes the aerosol source held in the wick 121Q or heats the flavor source held in the wick 121Q. The load 121R is constructed, for example, by use of a resistance heating element (for example, a heating wire) which is wound around the wick 121Q.

The air taken from an inflow hole 122A passes through a space near the load 121R in the atomizing unit 120. The inhalation component generated by the load 121R flows, together with the air, in the direction toward the inhalation port.

The aerosol source may be liquid at normal temperature. For example, a polyhydric alcohol may be used as the aerosol source. The aerosol source itself may comprise a flavor source. Alternatively, the aerosol source may comprise a tobacco raw material or an extract originated from a tobacco raw material, which releases a fragrance-inhaling-taste component when it is heated.

With respect to the above embodiment, an example relating to an aerosol source, which is liquid at normal temperature, has been explained; however, it is possible to use, in place of the above aerosol source, an aerosol source which is solid at normal temperature.

The atomizing unit 120 may comprise a flavor unit 130 which is configured to be exchangeable. The flavor unit 130 may comprise a cylindrical body 131 for storing a flavor source. The cylindrical body 131 may comprise a membrane member 133 and a filter 132. The flavor source may be arranged in a space constructed by the membrane member 133 and the filter 132.

The atomizing unit 120 may comprise a breaking unit 90. The breaking unit 90 is a member for breaking a part of the membrane member 133 in the flavor unit 130. The breaking unit 90 is held by a partition member 126 which separates the atomizing unit 120 from the flavor unit 130. For example, the partition member 126 comprises a polyacetal resin. For example, the breaking unit 90 is a cylindrical hollow needle. By piercing the membrane member 133 with a tip of the hollow needle, an air flowing path, that causes the atomizing unit 120 and the flavor unit 130 to communicate with each other to communicate air, is formed. In this regard, it is preferable that a mesh, which has a roughness that does not allow the flavor source passing through the mesh, be formed in the inside of the hollow needle.

According to an example of a preferred embodiment, the flavor source in the flavor unit 130 adds a fragrance-inhaling-taste component to aerosol generated by the load 121R in the atomizing unit 120. The flavor added by the flavor source to the aerosol is conveyed to the inhalation port of the inhalation component generation device 100. In this manner, the inhalation component generation device 100 may comprise plural inhalation component sources. Alternatively, the inhalation component generation device 100 may comprise a single inhalation component source.

The flavor source in the flavor unit 130 may be solid at normal temperature. For example, the flavor source comprises a raw-material piece of plant material which provides aerosol with a fragrance-inhaling-taste component. Regarding a raw-material piece which is a component of the flavor source, shredded tobacco or a product, which is made by processing tobacco material such as s tobacco raw material to have a granular form, may be used as the raw-material piece. Alternatively, the flavor source may comprise a product which is made by processing tobacco material to have a sheet form. Further, the raw-material piece, which is a component of the flavor source, may comprise a plant other than tobacco (for example, mint, a herb, and so on). The flavor source may be provided with flavor such as menthol or the like.

The inhalation component generation device 100 may comprise a mouthpiece 142 which has an inhalation port 141 for allowing a user to inhale an inhalation component. The mouthpiece 142 may be constructed in such a manner that it is attachable/detachable to/from the atomizing unit 120 and the flavor unit 130, or it is integrated with them to be inseparable.

The electric equipment unit 110 may comprise an electric power source 10, an inhalation sensor 20, a push button 30, a notification unit 40, and control unit 50. The electric power source 10 stores electric power required for operation of the flavor inhaler 100. The electric power source 10 may be attachable/detachable to/from the electric equipment unit 110. The electric power source 10 may be a rechargeable battery such as a lithium-ion secondary battery, for example.

When the atomizing unit 120 is connected to the electric equipment unit 110, the load 121R in the atomizing unit 120 is electrically connected to the electric power source 10 in the electric equipment unit 110 (refer to FIG. 5).

The inhalation component generation device 100 may comprise a switch 140 for electrical connection/disconnection between the load 121R and the electric power source 10. The switch 140 is opened/closed by the control unit 50. The switch 140 may comprise a MOSFET, for example.

If the switch 140 is turned on, electric power is supplied from the electric power source 10 to the load 121R. On the other hand, if the switch 140 is turned off, supply of electric power from the electric power source 10 to the load 121R is stopped. Turning on/off of the switch 140 is controlled by the control unit 50.

The control unit 50 may comprise an activation request sensor for detecting an action relating to a user's request for activation. The activation request sensor may be a push button 30 which is to be pushed by a user, or an inhalation sensor 20 for detecting an inhaling action of a user, for example. The control unit 50 obtains an operation request signal to the load 121R, and generates an instruction for operating the load 121R. In a tangible example, the control unit 50 outputs, to the switch 140, an instruction for operating the load 121R, and the switch 140 is turned on in response to the instruction. In this manner, the control unit 50 is configured to control supply of electric power from the electric power source 10 to the load 121R. If electric power is supplied from the electric power source 10 to the load 121R, the inhalation component source is vaporized or atomized by the load 121R.

Further, the inhalation component generation device 100 may comprise, as necessary, at least one of a voltage sensor 150, a current sensor 152, and a temperature sensor 154. It should be reminded that the temperature sensor 154 is not shown in FIG. 5 and FIG. 6, for convenience.

The voltage sensor 150 may be configured to be able to detect the voltage of the electric power source 10. The current sensor 152 may be configured to be able to detect the amount of current flown out of the electric power source 10, and the amount of current flown into the electric power source 10. The temperature sensor 154 may be configured to be able to detect temperature around the electric power source 10, for example. The control unit 50 may be configured to be able to obtain outputs from the voltage sensor 150, the current sensor 152, and the temperature sensor 154. The control unit 50 performs various control processes by use of the above outputs.

The inhalation sensor 20 is a sensor for outputting a value (for example, a voltage value or a current value) that changes according to the amount of the flow of air that is sucked in the direction from the non-inhalation-port side to the inhalation-port side (that is, the puff action performed by a user). Examples of such sensors that can be listed are a condenser microphone sensor, a publicly known flow sensor, and so on.

FIG. 3 shows a tangible example of the inhalation sensor 20. The inhalation sensor 20 exemplified in FIG. 3 comprises a sensor main body 21, a cover 22, and a circuit board 23. The sensor main body 21 comprises a capacitor, for example. The electric capacitance of the sensor main body 21 changes according to vibration (pressure) generated by air sucked from an air introducing hole 125 (that is, the air sucked in the direction from the non-inhalation-port side to the inhalation-port side). The cover 22 is installed on the sensor main body 21 at the inhalation-port side thereof, and has an opening 11A. By installing the cover 22 having the opening 22A, the electric capacitance of the sensor main body 21 is made to be more easily changeable, so that the response characteristic of the sensor main body 21 is improved. The circuit board 23 outputs a value (in this case, a voltage value) representing the electric capacitance of the sensor main body 21 (the capacitor).

The inhalation component generation device 100, more specifically, the electric equipment unit 110, is constructed in such a manner that it is connectable to a charger 200 for charging the electric power source 10 in the electric equipment unit 110 (refer to FIG. 6). When the charger 200 is connected to the electric equipment unit 110, the charger is electrically connected to the electric power source 10 in the electric equipment unit 110.

The electric equipment unit 110 may comprise a judgment unit for judging whether the charger 200 is being connected. For example, the judgment part may be a means for judging whether or not the charger 200 is being connected, based on change in a potential difference between a pair of electric terminals to which the charger 200 is connected. The judgment means is not limited to the above means, that is, the judgment means can be any means that can judge whether or not the charger 200 is being connected.

The charger 200 comprises an external electric power source 210 for charging the electric power source 10 in the electric equipment unit 110. The inhalation component generation device 100 may be communicable with a processor 250 in the charger 200. The processor 250 may be configured to be able to control at least one of discharging from the electric power source 10 to the external electric power source 210 and charging to the electric power source 10 from the external electric power source 210. Further, the charger 200 may comprise a current sensor 230 for obtaining a value of charging current and a voltage sensor 240 for obtaining a value of a charging voltage.

The control unit 50 may comprise a counter 52 for counting the number of times of detected puff actions that are performed by a user. Further, the control unit 50 may comprise a timer 54 for measuring time that has elapsed since the time that a user's puff action is detected, i.e., the time that an operation requesting signal to the load 121R is obtained.

The notification unit 40 performs a notification for notifying of a user of various kinds of information. The notification unit 40 may be a light emitting element such as an LED, for example. Alternatively, the notification unit 40 may be an element which outputs sound, or a vibrator. The control unit 50 may be configured to be able to control the notification unit 40 to operate in one of a normal use mode, a charge requesting mode, and an abnormality notifying mode. Regarding the normal use mode, the charge requesting mode, and the abnormality notifying mode, they will be explained later.

In the case that the notification unit 40 comprises a light emitting element, it is preferable that the light emitting element be positioned at a side face 124 which extends between the inhalation end E1 and the non-inhalation end E2 (refer to FIG. 1). In such a case, it is preferable to set the length from the inhalation end E1 to the light emitting element to that equal to or greater than 58 mm, and it is more preferable to set the length to that equal to or greater than 100 mm. Further, it is preferable to set the length from one end E1 to the other end E2 to that equal to or less than 135 mm.

Alternatively, the light emitting element may be arranged across the non-inhalation end E2 and a part of the side face 124 extending between the inhalation end E1 and the non-inhalation end E2 of the inhalation component generation device 100. In such a case, it is preferable to set the length from one end E1 to the other end E2, i.e., the approximate length from the inhalation end E1 to the light emitting element, to that equal to or greater than 58 mm, and it is more preferable to set the length to that equal to or greater than 100 mm. Further, it is preferable to set the length from one end E1 to the other end E2 to that equal to or less than 135 mm. The above length may be set, from a perspective of modeling after a shape of a widely distributed cigarette, or a perspective of visibility that the notification unit 40 enters a field of view of a user when the end E1 is held in the user's mouth.

As a result, a distance from an eye of a user to the other end E2 of the inhalation component generation device 100, i.e., to the light emitting element, can be secured, when a user holds the inhalation end E1 in the user's mouth and uses the inhalation component generation device 100. In the case that it is supposed that the distance between eyes of a general user is 100 mm, peripheral vision is taken into consideration, and the light emitting element emits purple color light, the user can begin recognition of the color of the light emitting element even if the user's line of sight is directed to a front center part, if the length from the inhalation end E1 to the light emitting element is equal to or greater than 58 mm. That is, it becomes easier to recognize difference between colors of the light emitting element, even if the user does not keep an eye on the light emitting element. Further, in the case that the distance from the inhalation end E1 to the light emitting element is set to that equal to or greater than 100 mm, the rate that the user recognizes the purple color exceeds 50%. It should be reminded that recognition of colors means that a specific color can be discriminated from other colors. In this regard, it is not necessarily required to be able to distinguish colors in a similar color group, and it is sufficient if plural colors, that are not in a similar color group and are easy to distinguish, can be distinguished.

In this regard, it should be reminded that the value of the above explained length that allows a user to be able to begin recognition of the color of the light emitting element, and the value of the length that causes the user's recognition rate with respect to the color to exceed 50% are values in an example wherein the light emitting element emits purple color light. In other words, the length from the inhalation end E1 to the light emitting element may be determined based on a specific color, in colors of light emitted from the light emitting element, that is expected to be recognized by a user.

Further, in the case that the light emitting element is positioned in a part of the side face 124 extending between the inhalation end E1 and the non-inhalation end E2, there is a merit that it is easier for a user to recognize the color of the light emitting element under a state that the user is holding the inhalation component generation device 100 in the user's mouth.

Figure 7:
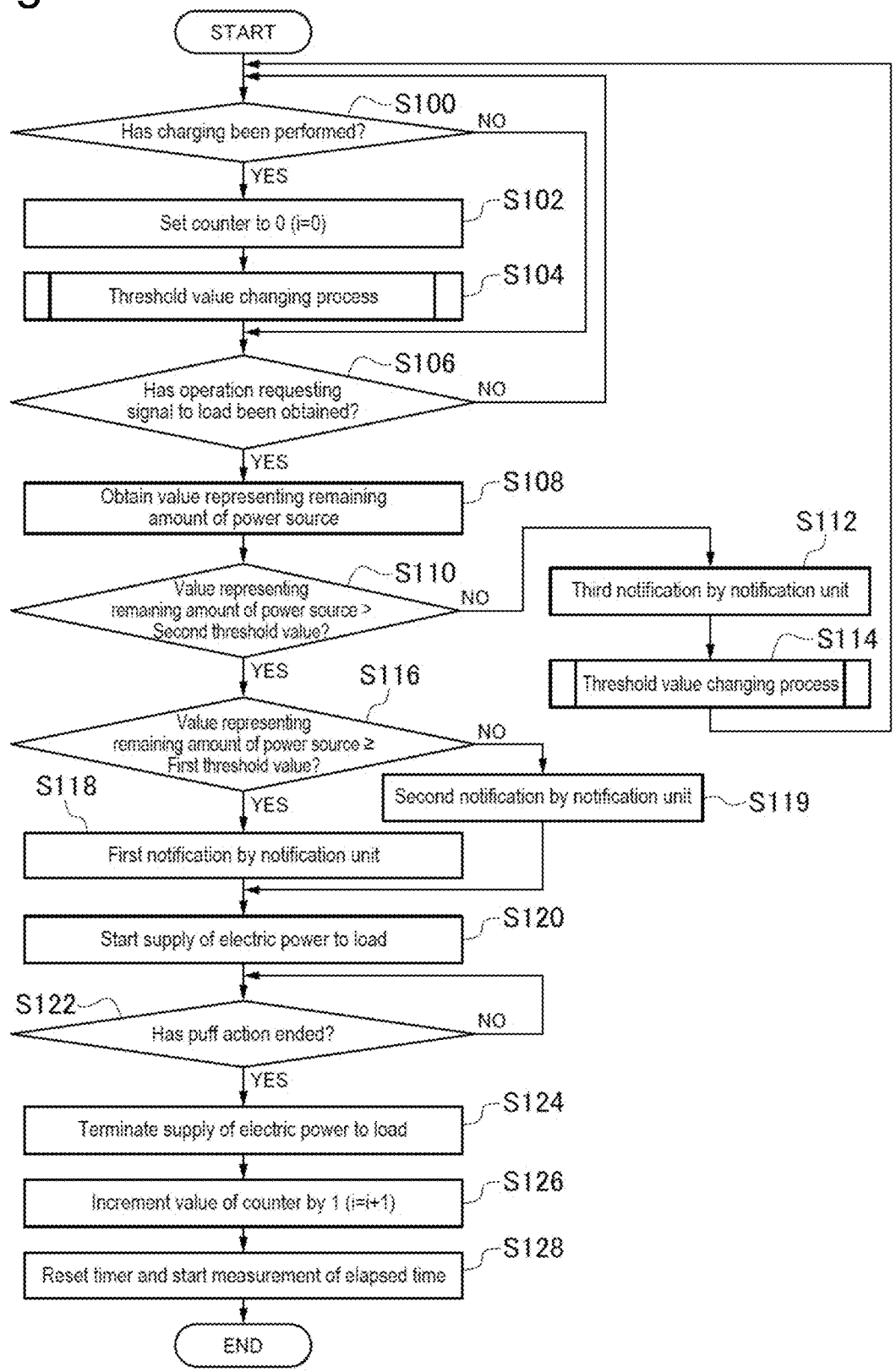
FIG. 7 is a flow chart showing an example of a method for controlling an inhalation component generation device.
Figure 8:
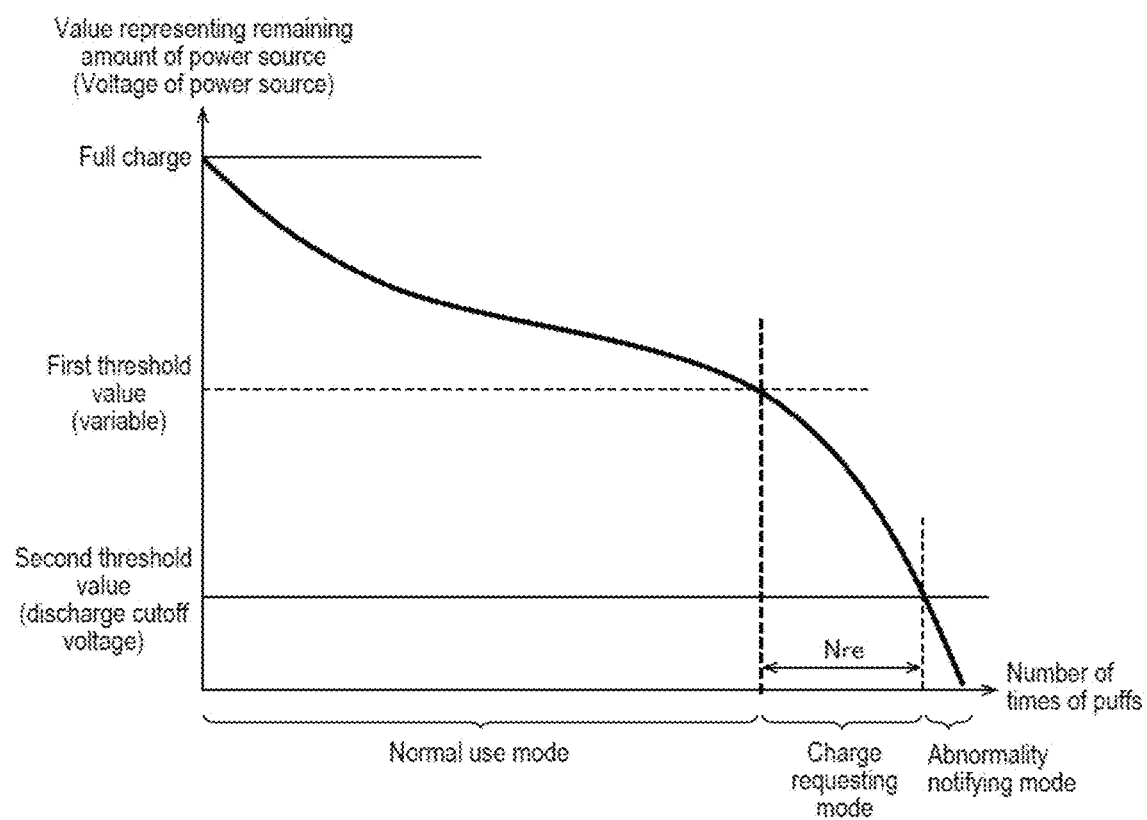
FIG. 8 is a graph showing relationship between the number of times of puff actions performed by a user and a value showing a remaining amount of an electric power source.

FIG. 7 is a flow chart showing an example of a method for controlling an inhalation component generation device. FIG. 8 shows relationship between the number of times of puff actions performed by a user and a value showing a remaining amount of an electric power source.

During the following series of processes, it is preferable that the counter 52 measure the number of times of puff actions performed by a user.

The control unit 50 monitors whether charging to the electric power source 10 by the charger 200 has been performed (step 100). Judgment with respect to whether charging has been performed may be performed by monitoring a value representing the remaining amount of the electric power source 10. For example, the control unit 50 can judge that charging has been performed, if the value representing the remaining amount of the electric power source 10 has been increased to a predetermined amount or more. Alternatively, it is possible to judge that charging has been performed, if the current sensor 152 installed in the electric equipment unit 110 detects charging current for charging the electric power source 10. Further, as an alternative to the above, it is possible to judge that charging has been performed, if information representing the state that charging from the charger 200 to the electric equipment unit 110 is being performed is being communicated by a communication means which is not shown in the figures and allows communication between electric equipment unit 110 and the charger 200. Still further, as an alternative to the above, it is possible to judge that charging has been performed, if a signal of a request for charging has been sent from the electric equipment unit 110 to the charger 200. In this regard, communication between the electric equipment unit 110 and the charger 200 may be performed by use of power line carrier communication (PLC) via circuits, without using a dedicated communication means.

The value representing the remaining amount of the electric power source 10 may be a voltage of the electric power source 10, a state of charge (SOC) of the electric power source 10, or a remaining capacity of the electric power source, for example. The voltage of the electric power source 10 may be an open circuit voltage (OCV) that is obtained without electrically connecting the load 121R to the electric power source 10, or a closed circuit voltage (CCV) that is obtained in the state that the load 121R is being electrically connected to the electric power source 10. In this regard, from a perspective of accuracy with respect to estimating of the remaining amount of the electric power source 10, it is preferable to use an open circuit voltage (OCV) rather than a closed circuit voltage (CCV), when determining the value representing the remaining amount of the electric power source 10, for eliminating effect due to voltage drop relating to electrical connection to the load 121R, change in internal resistance relating to discharging, and change in temperature.

In the case that charging has been performed, it is preferable that the control unit 50 set the value of the counter 52 to "0" (step S102). Then, the counter 52 can measure the number of times of puff actions since the time that charging has performed until the present time.

Further, in the case that charging has been performed, the control unit 50 may perform a threshold value changing process S104 as necessary. Regarding the threshold value changing process S104, it will be explained later in detail.

Further, the control unit 50 waits, until it obtains an operation requesting signal to the load 121R (step S106). The operation requesting signal to the load 121R is inputted from the above-explained activation request sensor to the control unit 50, in response to action of a user.

After obtaining the operation requesting signal to the load 121R, the control unit 50 obtains a value representing the remaining amount of the electric power source 10 (step S108). Examples of the value representing the remaining amount of the electric power source 10 are those explained in the above description. The obtained value representing the remaining amount of the electric power source 10 is stored in the memory 58.

If the obtained value representing the remaining amount of the electric power source 10 is less than a second threshold value, the control unit 50 controls the notification unit 40 in the abnormality notifying mode, and causes the notification unit 40 to perform a third notification (steps S110 and S112). The abnormality notifying mode is a mode representing a state that the remaining amount of the electric power source is 0 or extremely low so that the load 121R cannot normally generate inhalation components from the inhalation component source.

The second threshold value may be determined by using a value corresponding to the remaining amount of the electric power source that is 0 or close to 0, for example. In the case that the value representing the remaining amount of the electric power source 10 is the voltage of the electric power source 10, the second threshold value may be determined by using a discharge cutoff voltage or a voltage slightly larger than the discharge cutoff voltage, for example. In the case that the value representing the remaining amount of the electric power source 10 is a state of charge or a remaining capacity of the electric power source 10, the second threshold value may be determined by using a state of charge or a remaining capacity corresponding to a discharge cutoff voltage or a voltage slightly larger than the discharge cutoff voltage, for example.

In the abnormality notifying mode, the control unit 50 may wait, without supplying electric power to the load 121R. Alternatively, after entering the abnormality notifying mode, the control unit 50 may turn off the inhalation component generation device 100 automatically.

Preferably, after entering the abnormality notifying mode, the control unit 50 performs the threshold value changing process as necessary (step S114). Details of the threshold value changing process S114 will be explained later.

In the case that the obtained value representing the remaining amount of the electric power source 10 is equal to or greater than a first threshold value that is greater than the second threshold value, the control unit 50 controls, in the normal use mode, the notification unit 40 to perform a first notification (steps S110, S116, and S118). The normal use mode is a mode wherein the remaining amount of the electric power source 10 is sufficiently large so that the load 121R can generate inhalation components from the inhalation component source. The first threshold value is used for distinguishing the normal use mode from a charge requesting mode that will be explained later.

In the normal use mode, the control unit 50 obtains an operation requesting signal to the load 121R and generates an instruction for activating the load 121R. The switch 140 is turned on based on the above instruction, and electric power is supplied thereby to the load 121R (step S120). As a result, the load 121R generates inhalation components from the inhalation component source. The generated inhalation components are inhaled by a user via the inhalation port. The control unit 50 may control the amount of electric power supplied to the load 121R by performing pulse width control (PWM).

After the control unit 50 has judged, based on the operation requesting signal from the activation request sensor, that an activation requesting action (an inhalation action) performed by a user is completed, the control unit 50 turns the switch 140 off to thereby stop supply of electric power to the load 121R (step S122 and S124). Further, in the case that the length of time that the user performs the activation requesting action (the inhalation action) exceeds a predetermined period of time, the control unit 50 may forcibly stop supply of electric power to the load 121R. The above predetermined period of time, that is used when forcibly stopping supply of electric power to the load 121R, may be set based on a period of time of a usual single inhalation action performed by a user, so that the predetermined period of time may be set to time in the range between 2-4 seconds, for example.

After the control unit 50 has detected, based on the operation requesting signal from the activation request sensor, a puff action performed by a user, the control unit 50 increments the value of the counter 52, which measures the number of times of puff actions, by 1. Further, the control unit 50 resets the timer 54, and measures elapsed time by use of the timer 54 (step S128). Thus, the control unit 50 can measure the leaving time, that is a period during that electric power is not supplied to the load 121R, by use of the timer 54.

The state returns to the waiting state after stopping of electric power to the load 121R, and the control unit 50 again performs monitoring to judge whether charging has been performed (step S100), and whether an operation requesting signal to the load 121R has been obtained (step S106).

If the value, that has been obtained in step S108 and represents the remaining amount of the electric power source, is less than the first threshold value and equal to or greater than the second threshold value, the control unit 50 controls, in the charge requesting mode, the notification unit 40 to perform a second notification (steps S110, S116 and S119). The charge requesting mode has been prepared for notifying a user of a decrease in the remaining amount of the electric power source 10 and requesting that a user perform charging, although generation of inhalation components by supplying electric power to the load 121R is still possible.

In the charge requesting mode, the control unit 50 also obtains an operation requesting signal to the load 121R and generates an instruction for activating the load 121R, in a manner similar to that in the case of the normal use mode. The switch 140 is turned on based on the above instruction, and electric power is supplied thereby to the load 121R (step S120). As a result, the load 121R generates inhalation components from the inhalation component source. As explained above, the beginning to the last of the steps for supplying electric power to the load 121R (steps S120, S122, and S124) in the charge requesting mode can be performed in a manner similar to that in the case of the normal use mode. Further, the control unit 50, when it has detected a user's puff action, also increments the value of the counter 52 by 1, in the charge requesting mode (step S126). Further, the control unit 50 resets the timer 54, and measures elapsed time by use of the timer 54 (step S128). Thus, the control unit 50 can measure the leaving time, that is a period during that electric power is not supplied to the load 121R, by use of the timer 54.

The above-explained first threshold value is a variable value that can be changed based on the operation requesting signal that is directed to the load 121R and obtained by the control unit 50. That is, the condition to switch between the normal use mode and the charge requesting mode is changed based on the operation requesting signal. Changing of the first threshold value is automatically performed by the control unit 50 in the above-explained threshold value changing process, for example. Preferably, the first threshold value is changed based on a value relating supply of electric power from the electric power source 10 to the load 121R. The value relating to the above supply of electric power may be a voltage of the electric power source 10, a state of charge of the electric power source 10, or a remaining capacity of the electric power source, or the like, for example. More specifically, the first threshold value may be changed based on a amount of voltage drop of the electric power source 10 per single puff, a amount of decrease in the state of charge of the electric power source 10 per single puff, or a amount of decrease in the remaining capacity of the electric power source 10 per single puff, for example.

In this regard, the curve, that is shown in FIG. 8 and represents relationship between the value representing the remaining amount of the electric power source and the number of times of puff actions, changes depending on the way that a puff action is performed (inhalation time and inhalation amount), the degree of deterioration of the electric power supply, and so on.

The operation requesting signal outputs a signal corresponding to the way to use by a user. For example, the inhalation sensor 20 outputs an output signal (an operation requesting signal) corresponding to an inhalation amount and inhalation time per single puff of a user (refer to the graphs in FIG. 9 and the upper part of FIG. 10).

Thus, in the case that the first threshold value is changeable based on an operation requesting signal to the load 121R, for example, based on a value relating to supply of electric power to the load 121R, the first threshold value is made to be changeable to correspond to the way to use of the load 121R. As a result, the timing to notify of the second notification is made to be changeable to correspond to the way to use of the inhalation component generation device by a user. Thus, according to the present embodiment, it becomes possible to notify of the second notification at more appropriate timing, to correspond to the way to use of the inhalation component generation device by a user.

(Embodiments of Notifications Issued by the Notification Unit)

The above-explained first notification, second notification and third notification are different from each other. That is, in the above-explained embodiment, notifications from the notification unit 40 in the normal use mode, the charge requesting mode, and the abnormality notifying mode are different from each other. Thus, by use of at least three kinds of notifications corresponding to the remaining amounts of the electric power source 10, the notification unit 40 can make a user able to recognize differences between the remaining amounts of the electric power source 10 and/or the modes.

Thus, the notification unit 40 can inform a user of differences between the normal use mode, the charge requesting mode, and the abnormality notifying mode, by notifying the user of notifications that are different from each other. An inhalation component generation device such as an electronic cigarette has to model after a shape, weight, and so on of a widely distributed cigarette, and, further, has to comprise, as necessary components, a reservoir 121P and a flavor unit 130 for storing or receiving an aerosol source and/or a flavor source, and parts that are difficult to be downsized such as the electric power source 10 and so on. Thus, restriction relating to a user interface (U/I) and layout (L/O) is especially strict. In such an inhalation component generation device, the notification unit 40 can effectively make a user able to recognize differences between the normal use mode, the charge requesting mode, and the abnormality notifying mode, by use of notifications that are different from each other, for example, by use of differences in appearances of notifications.

Further, by informing by the second notification, before performing the third notification, that the remaining amount of the electric power source 10 has been decreased, a notification for requesting charging of the electric power source 10 before exhausting the remaining amount of the electric power source 10 can be given to a user. In this regard, it has been known that deterioration of the electric power source 10 is accelerated if the remaining amount of the electric power source 10 is exhausted. According to the present embodiment, accelerating of deterioration of the electric power source 10 can be prevented, by encouraging charging of the electric power source 10 before the remaining amount of the electric power source 10 is exhausted.

It is preferable that the notification unit 40 comprise a light emitting element. In such a case, the first notification, the second notification, and the third notification may comprise a first light emission color, a second light emission color, and a third light emission color by the light emitting element, respectively. In this regard, the first light emission color, the second light emission color, and the third light emission color are different from each other.

More preferably, the first light emission color includes a cold color, the second light emission color includes an intermediate color, and the third light emission color includes a warm color. In this regard, the "intermediate color" used as the second light emission color is determined as a color between the "cold color" used as the first light emission color and the "warm color" used as the third light emission color in a hue circle.

The "hue circle" is determined by using a hue circle that is constructed by arranging hues in the Munsell color system to have an annular shape. The "warm color" may be determined based on a region having hue of 10 RP-10 Y in the Munsell color system, or light having an optical spectral peak in a wavelength range of 570 nm-830 nm. For example, red can be exemplified as the "warm color." The "cold color" may be determined based on a region having hue of 5 BG-5 PB in the Munsell color system, or light having an optical spectral peak in a wavelength range of 450 nm-500 nm. For example, blue can be exemplified as the "cold color." The "intermediate color" may be determined based on a region having hue of 5 PB-10 RP in the Munsell color system, or light having an optical spectral peak in a wavelength range of 380 nm-450 nm. For example, purple can be exemplified as the "intermediate color."

By making the third light emission color in the abnormality notifying mode to include a warm color, it becomes possible to effectively impress a user a state that an abnormal event has occurred, specifically, a state that the remaining amount of the electric power source 10 has been exhausted. On the other hand, by making the first light emission color in the normal use mode to include a cold color, it becomes possible to impress a person that the inhalation component generation device 100 is being operated without any problems. Further, by making the second light emission color in the charge requesting mode to be an intermediate color between the first light emission color and the third light emission color, it becomes possible to effectively impress a user that the mode is transitioning from the normal use mode, wherein the remaining amount of the electric power source 10 is sufficiently large, to the abnormality notifying mode, wherein the remaining amount of the electric power source 10 has been exhausted.

Preferably, the distance between a complementary color of the first light emission color and the third light emission color on the hue circle is shorter than the distance between the complementary color of the first light emission color and the second light emission color on the hue circle. Alternatively, or additionally, it is preferable that the distance between a complementary color of the third light emission color and the first light emission color on the hue circle is shorter than the distance between the complementary color of the third light emission color and the second light emission color on the hue circle.

In this regard, a "complementary color" of a color means a color positioned opposite to the above color (in other words, positioned on a diagonal line) on the hue circle. A combination of a color and a complementary color thereof corresponds to a combination of colors that makes the colors noticeable each other. Thus, in the case that the third light emission color is closer, than the second light emission color, to the complementary color of the first light emission color in the hue circle, it becomes easier for a user to distinguish the third light emission color from the first light emission color. As a result, it becomes possible to effectively impress a user that the mode relating to the third light emission color is the mode opposite to the normal use mode that relates to the first light emission color, i.e., the abnormality notifying mode.

Further, the wavelength of light corresponding to the second light emission color may be set to a wavelength that is closer to the wavelength of light corresponding to the first light emission color than the wavelength of light corresponding to the third light emission color. Especially, in the case that the light emitting element is that having a protruding optical spectral peak in a specific wavelength range, for example, an LED or the like, it is preferable that the wavelengths of light of the respective emission colors satisfy the above relationship.

In a preferred example, the first notification is constructed by use of blue light outputted from the light emitting element, the second notification is constructed by use of purple light outputted from the light emitting element, and the third notification is constructed by use of red light outputted from the light emitting element.

Figure 9:
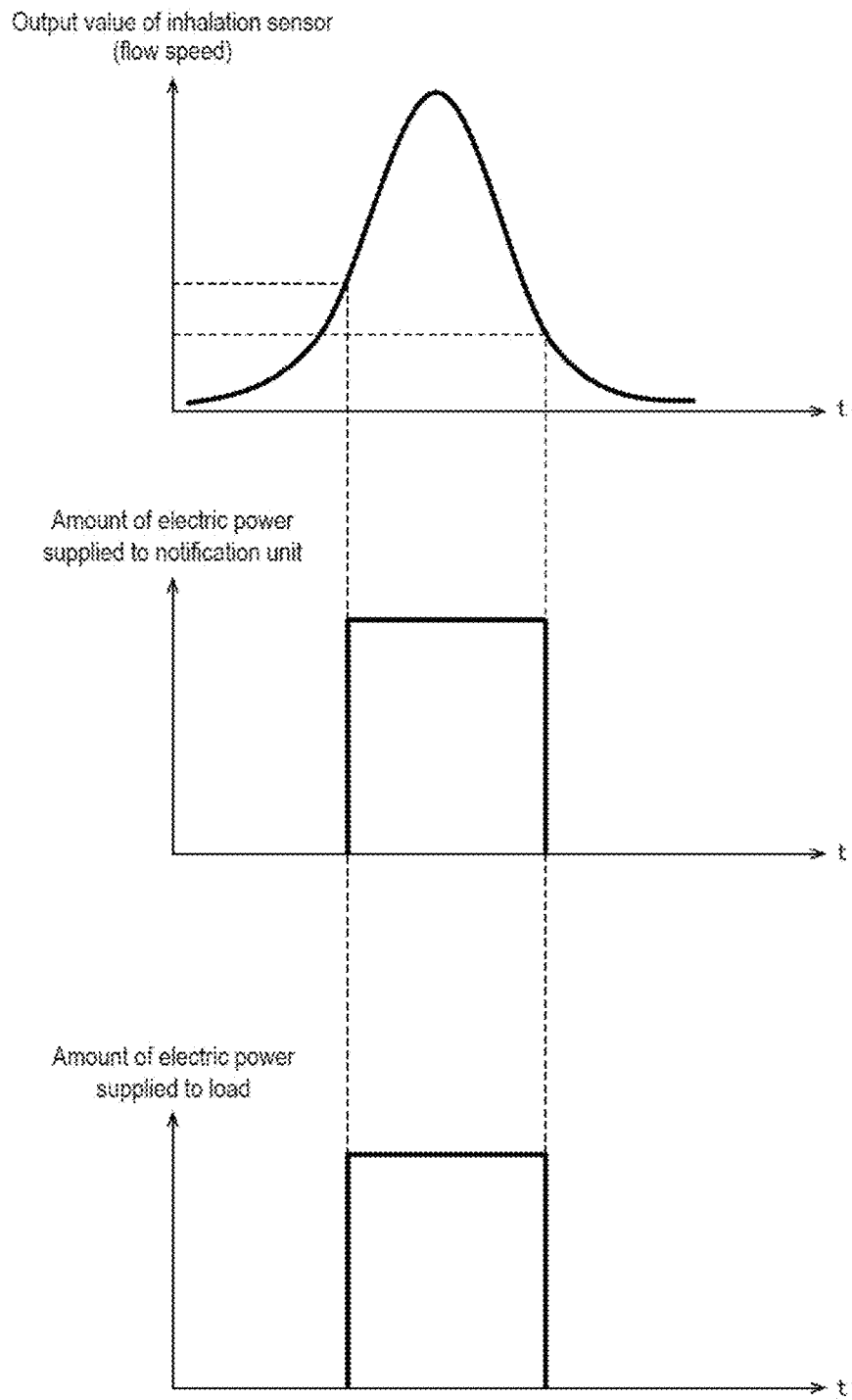
FIG. 9 is a figure showing an example of a light emitting pattern of a light emitting element in a normal use mode and a charge requesting mode.
Figure 10:
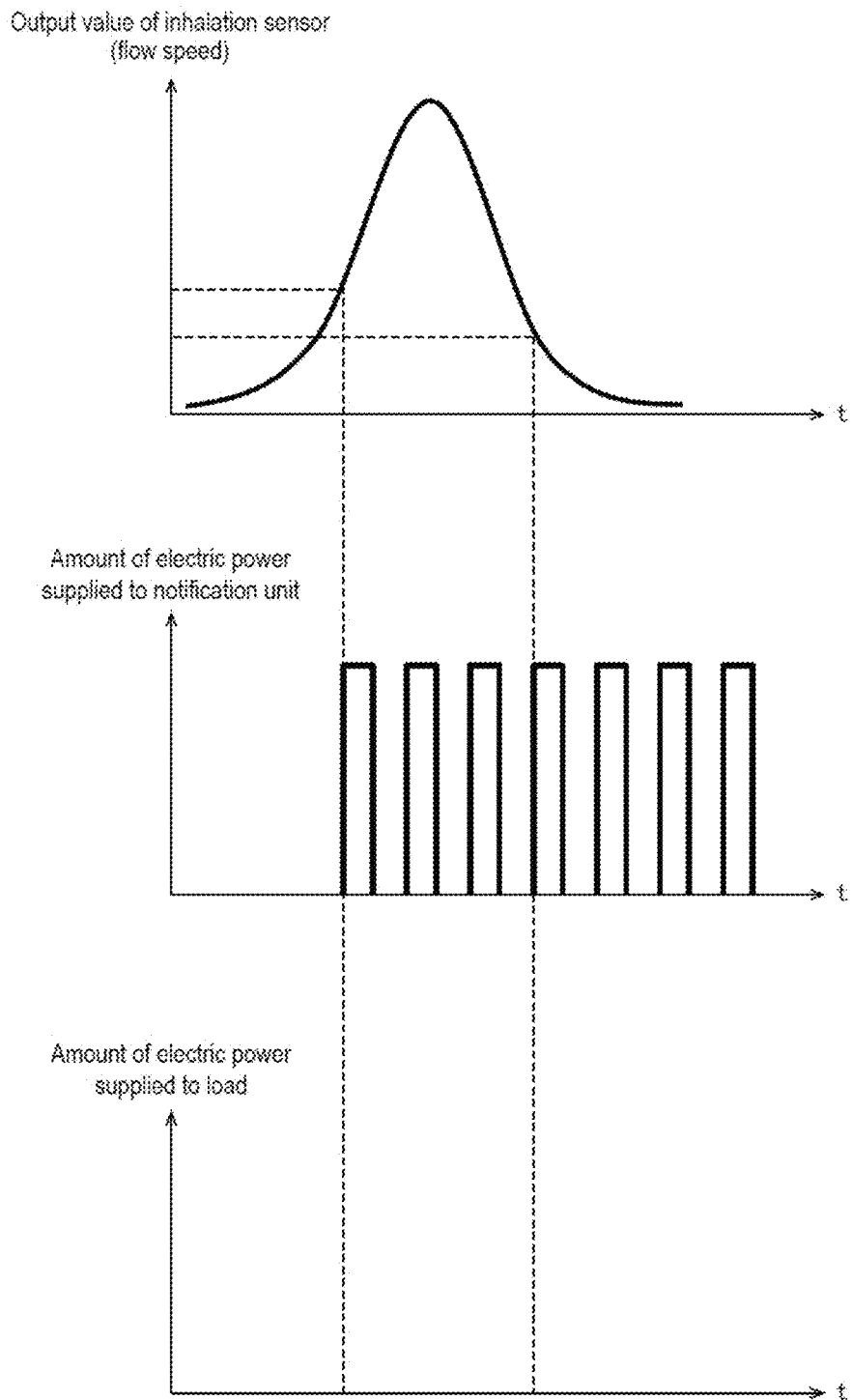
FIG. 10 is a figure showing an example of a light emitting pattern of a light emitting element in an abnormality notifying mode.

Next, examples of light emitting patterns of the light emitting element will be explained with reference to FIG. 9 and FIG. 10. FIG. 9 is a figure showing an example of a light emitting pattern of a light emitting element in the normal use mode and the charge requesting mode. FIG. 10 is a figure showing an example of a light emitting pattern of a light emitting element in the abnormality notifying mode. In each of FIG. 9 and FIG. 10, the graph in the upper part thereof shows time dependency of the output value of an operation request sensor, for example, the inhalation sensor 20. In each of FIG. 9 and FIG. 10, the graph in the middle part thereof shows time dependency of supply of electric power to the light emitting element. In each of FIG. 9 and FIG. 10, the graph in the lower part thereof shows time dependency of supply of electric power to the load 121R.

In each of the normal use mode, the charge requesting mode, and the abnormality notifying mode, the light emitting element may emit light always, or may be made to be blinked by repeating light-emission and non-light-emission. In the illustrated example, the light emitting element emits light for a desired period of time, in the normal use mode and the charge requesting mode. On the other hand, in the abnormality notifying mode, the light emitting element repeats light-emission and non-light-emission.

The control unit 50 may cause the light emitting element to start, by using the operation requesting signal as a trigger, light emission in each of the normal use mode, the charge requesting mode, and the abnormality notifying mode. For example, in the case that the operation request sensor is the inhalation sensor 20 which outputs a value relating to a flow velocity in the inhalation component generation device 100, the control unit 50 may start supply of electric power to the light emitting element and cause the light emitting element to emit light, when the output value of the inhalation sensor 20 exceeds a predetermined threshold value, as shown in FIG. 9 and FIG. 10.

Further, in the normal use mode and the charge requesting mode, the control unit 50 may cause the light emitting element to stop light emission when it has judged that an activation requesting action (an inhalation action) of a user is completed. For example, in the case that the operation request sensor is the inhalation sensor 20 which outputs a value relating to a flow velocity in the inhalation component generation device 100, the control unit 50 may stop supply of electric power to the light emitting element and cause the light emitting element not to emit light, when the output value of the inhalation sensor 20 decreases to a value below the other predetermined threshold value, as shown in FIG. 9. That is, the control unit 50 controls the length of the period of each of the first notification and the second notification performed by the notification unit 40 to vary, according to the length of the period that the operation requesting signal from the inhalation sensor 20 is continuously obtained. In the above description, a method for controlling the notification unit 40 based on the operation requesting signal from the inhalation sensor 20 is explained; however, the operation requesting signal may be outputted from a sensor other than the inhalation sensor 20. For example, in the case that the push button 30 is used, the control unit 50 controls the length of the period of each of the first notification and the second notification performed by the notification unit 40 to vary, according to the length of the period that the operation requesting signal from the push button 30 is continuously obtained.

It is preferable that the light emitting pattern of the light emitting element for the first notification in the normal use mode and that for the second notification in the charge requesting mode be the same (refer to FIG. 9). Specifically, at least one of, or preferably both, the notification timing and the notification period of the first notification, when the control unit 50 has detected the operation requesting signal, may be the same as that/those of the second notification. By setting the notification pattern (light emitting pattern) of the first notification to be the same as that of the second notification while the emission color for the second notification has been set to be different from the emission color for the first notification, it becomes possible to enable a user to be able to easily recognize, from the second notification, that an inhalation component can be generated from an inhalation component source in the charge requesting mode in a manner similar to that in the normal use mode relating to the first notification.

Further, as shown in FIG. 9, the timing to start and the timing to terminate the first notification performed by the notification unit 40 may be the same as the timing to start and the timing to terminate supply of electric power to the load 121R.

Alternatively, the timing to terminate the second notification in the charge requesting mode may be longer than the timing to terminate supply of electric power to the load 121R, preferably, the timing to terminate a puff action.

The control unit 50 may be configured to control the notification unit 40 to perform the third notification for a predetermined period that is independent of the period that the operation requesting signal is continuously obtained (refer to FIG. 10). That is, the notification unit 40 may perform the third notification for a predetermined period, without being affected by the time of a puff action performed by a user. In this case, it is preferable that the period that each of the first notification and the second notification is performed by the notification unit be set to a time period shorter than the above predetermined period for performing the third notification. For example, the predetermined period that the third notification is performed may be set to a time period longer than the period of a usual single inhalation action of a user, for example, a time period in the range of 4.5-6 seconds.

By the above embodiment, it becomes easier to distinguish the third notification in the abnormality notifying mode from the first notification in the normal use mode and the second notification in the charge requesting mode. Further, since the third notification is performed for a period longer than the periods of the first notification in the normal use mode and the second notification in the charge requesting mode, a user is effectively notified of a state that charging is necessary.

It should be reminded that, in the present embodiment, the construction wherein the first notification in the normal use mode is constructed by use of blue light outputted from the light emitting element, the second notification in the charge requesting mode is constructed by use of purple light outputted from the light emitting element, and the third notification in the abnormality notifying mode is constructed by use of red light outputted from the light emitting element has been explained. Instead of the above embodiment, the light emitting element may be constructed by use of plural emission colors in each notification. More specifically, even in a mode, emission color of the light emitting element may be changed according to the time elapsed since performing of each notification is started. Further, the light emitting element may emit plural emission colors at the same time.

That is, at least a part of the light emitting element is constructed by blue light during at least a part of the period of the first notification in the normal use mode, at least a part of the light emitting element is constructed by purple light during at least a part of the period of the second notification in the charge requesting mode, and at least a part of the light emitting element is constructed by red light during at least a part of the period of the third notification in the abnormality notifying mode.

(The Threshold Value Changing Process)

Figure 11:
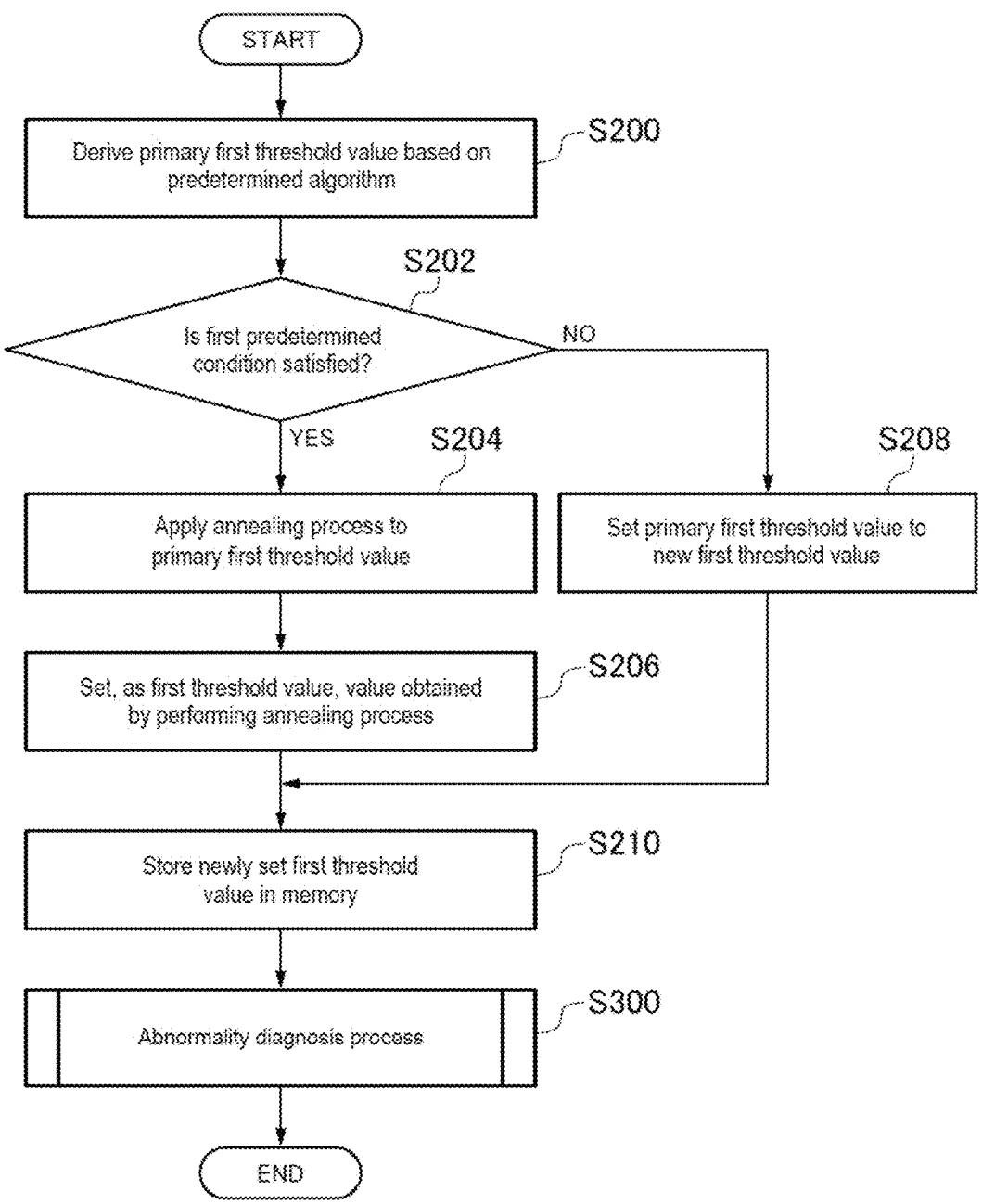
FIG. 11 is a flow chart showing an example of a threshold value changing process.

The above-explained threshold value changing process will be explained in detail. FIG. 11 shows an example of a flow chart of a threshold value changing process. When the value representing the remaining amount of the electric power source 10 is decreased to a value equal to or less than the second threshold value, it is preferable that the control unit 50 perform the threshold value changing process S114.

Figure 12:
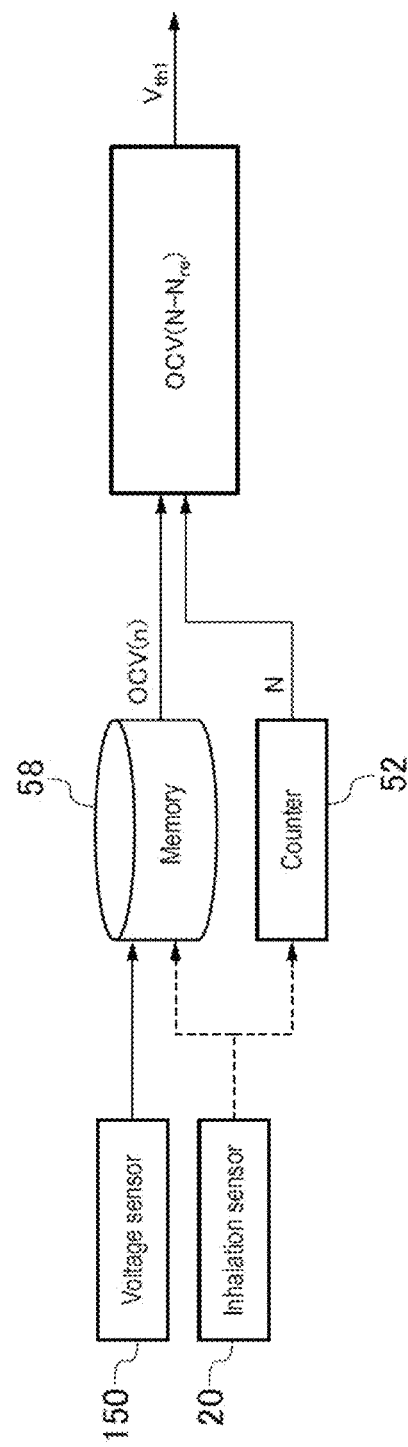
FIG. 12 is an example of a block diagram of a control unit for implementing a predetermined algorithm.

In the threshold value changing process, a primary first threshold value is derived based on a predetermined algorithm (step S200). FIG. 12 shows a block diagram of a control unit for implementing a predetermined algorithm relating to this example.

In the example shown in FIG. 12, the value representing the remaining amount of the electric power source 10 is determined by using the voltage of the electric power source 10. In this case, a full charge state is determined by using a full charge voltage, and the second threshold value is determined by using a discharge cutoff voltage. Also, in this case, in the flow chart shown in FIG. 7, the control unit 50 obtains a voltage of the electric power source 10 as a value representing the remaining amount of the electric power source 10. It is preferable that the voltage of the electric power source 10 be an open circuit voltage (OCV) that is obtained in the state that the switch 140 is being turned off. The open circuit voltage (OCV) is stored in the memory 58 every time a puff action is performed.

The predetermined algorithm relating to this example is performed, when the voltage of the electric power source 10 has decreased to a value equal to or less than the discharge cutoff voltage. In the algorithm, the first threshold value is changed based on a voltage value of the electric power source 10 when the load is operated at timing that is, in terms of the number of times of operations, a predetermined number of times of operations before the time that the voltage of the electric power source 10 reaches the discharge cutoff voltage. Specifically, the control unit 50 obtains, from the memory 58, a voltage (OCV(N–$N_{re}$)) of the electric power source 10 obtained at timing that is a predetermined number of times ($N_{re}$) of puff actions before the number of times (N) of puff actions measured after charging is completed, and sets the voltage as the primary first threshold value (refer to FIG. 12).

In the case that a first predetermined condition is not satisfied, the control unit 50 sets the primary first threshold value to a new first threshold value (steps S202 and S208). In the case that the first predetermined condition is satisfied, the control unit 50 sets the first threshold value to a value obtained by apply an annealing process to the primary first threshold value (steps S202, S204, and S206). In this regard, the first predetermined condition is a condition that the state of deterioration of the electric power supply 10 has not yet progressed beyond a predetermined judgment state, that will be explained later, for example. The annealing process will be explained later.

The predetermined number of times ($N_{re}$) may be a preset fixed value, or a variable value that is settable by a user. In a tangible example, although there is no specific limitation, the predetermined number of times ($N_{re}$) is, preferably, 15-35 times, and, more preferably, 20-30 times.

It is preferable that the predetermined number of times ($N_{re}$) be smaller than the number of times that an unused inhalation component source can be used. In the case that the inhalation component generation device 100 comprises plural inhalation component sources, it is more preferable that it be smaller than the minimum number of times in the plural numbers of times that plural inhalation component sources can be used respectively. For example, in the case that the inhalation component generation device 100 comprises the atomizing unit 120 and the flavor unit 130, the predetermined number of times may be set to a value smaller than a smaller one of the number of times that the atomizing unit 120 can be used and the number of times that the flavor unit 130 can be used.

In this regard, the usable numbers of times may be values that are set in advance according to design of the atomizing unit 120 and the flavor unit 130. For example, the usable number of times may be a maximum usable number of times when the amount of smoke inhaled per puff is within the scope of design of each inhalation component source in advance, or a maximum usable number of times when components inhaled per puff is within the scope of design.

By setting the predetermined number of times ($N_{re}$) to be smaller than the number of times that an unused inhalation component source can be used, it becomes possible to prevent timing to change the atomizing unit 120 or the flavor unit 130 from occurring during the charge requesting mode. Thus, it becomes possible to suppress overruling of the understanding that a predetermined number of times of puff actions, roughly, are allowed in the charge requesting mode.

It is preferable that the control unit 50 performs, as necessary, an annealing process for making the primary first threshold value derived by the predetermined algorithm to be a value closer to at least one of previously changed plural first threshold values (step S204). In this case, the control unit 50 sets the first threshold value based on a value derived by performing the annealing process (step S206).

In this regard, it is preferable that the first threshold value be stored in the memory 58 every time it is changed (step S210). That is, the memory 58 stores history of the first threshold value. By the above-explained threshold value changing process, the value of the first threshold value used in the flow chart shown in FIG. 7 is changed.

If the first threshold value is changed, it is preferable that an abnormality diagnosis process S300 be performed as necessary. The abnormality diagnosis process S300 will be explained later.

By changing the first threshold value by the threshold value changing process relating to this example, it becomes possible to ensure that a predetermined number of times of puff actions can be performed until transitioning to the abnormality notifying mode from the charge requesting mode. That is, regardless of the way of a user's puff action (the pattern of the operation requesting signal) and/or deterioration of the electric power source 10, a predetermined number of times of puff actions that can be allowed during the charge requesting mode can be ensured. As a result, it becomes possible to prevent sudden inhibition of use of the inhalation component generation device 100 after entering the charge requesting mode, and provide a user with a highly convenient inhalation component generation device 100.

(The Other Example of the Predetermined Algorithm)

Figure 13:
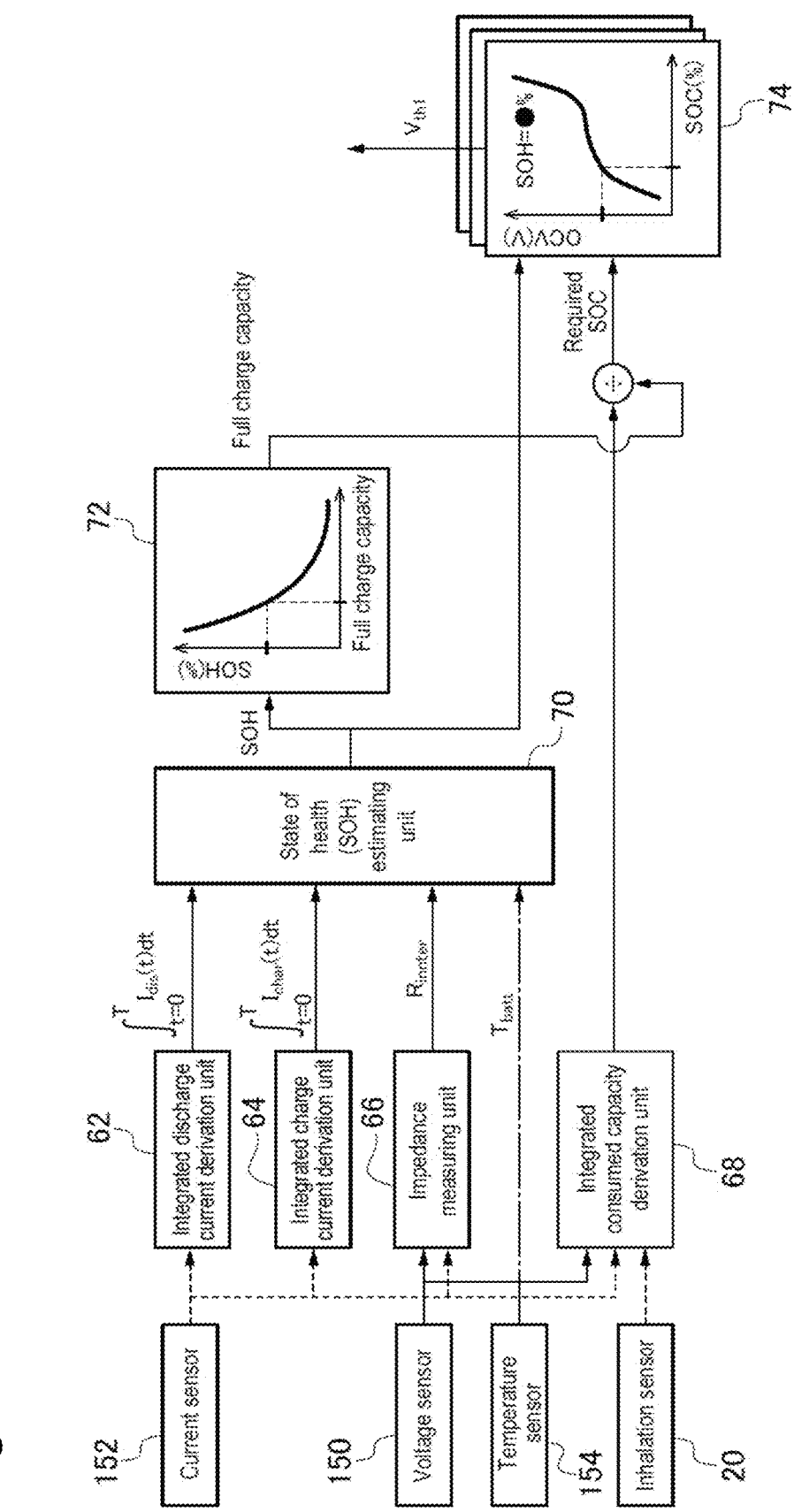
FIG. 13 is another example of a block diagram of a control unit for implementing a predetermined algorithm.

Next, another example of the predetermined algorithm will be explained. FIG. 13 is a block diagram of a control unit for implementing a predetermined algorithm relating to this example.

In the example shown in FIG. 13, the value representing the remaining amount of the electric power source 10 is determined by using a state of charge (SOC) or a remaining capacity of the electric power source 10. In this case, the second threshold value may be a state of charge or a remaining capacity of the electric power source when the voltage of the electric power source has become the discharge cutoff voltage. Also, in this case, in the flow chart shown in FIG. 7, the control unit 50 obtains, as a value representing the remaining amount of the electric power source 10, a state of charge or a remaining capacity of the electric power source 10. The obtained state of charge or the obtained remaining capacity is stored in the memory 58 every time a puff action is performed. Also, in the case that a state of charge (SOC) of the electric power source 10 is used as a value representing the remaining amount of the electric power source 10, the second threshold value in step S110 and the first threshold value in step S116 are made to be values that are appropriate for comparison with a state of charge (SOC), so that the dimension (unit) of each of the values is made to be (%). On the other hand, in the case that a remaining capacity of the electric power source 10 is used as a value representing the remaining amount of the electric power source 10, the first threshold value in step S110 and the second threshold value in step S116 are made to be values that are appropriate for comparison with a remaining capacity, so that the dimension (unit) of each of the values is made to be (Wh).

It is preferable that the predetermined algorithm relating to this example be performed when the state of charge of the electric power source 10 becomes a value equal to or less than a state of charge corresponding to the discharge cutoff voltage. In the algorithm, the first threshold value is changed based on a value obtained by adding, to the second threshold value, a state of charge or a remaining capacity of the electric power source 10 that is required for driving the load 121R for a amount corresponding to the above-explained predetermined number of times.

The state of charge (SOC) or the remaining capacity of the electric power source 10 can be estimated by a well-known SOC-OCV method, a current integration method (a coulomb count method), and so on, for example. FIG. 13 shows an example in which an SOC-OCV method is used. In the method, the control unit 50 comprises a state-of-health (SOH) estimating unit 70 for estimating the state of deterioration of the electric power source 10. Further, the control unit 50 comprises an integrated discharge current derivation unit 62, an integrated charge current derivation unit 64, an impedance measuring unit 66, and an integrated consumed capacity derivation unit 68. The integrated discharge current derivation unit 62 and the integrated charge current derivation unit 64 use the current sensor 152 to calculate an integrated value of current outputted from the electric power source 10 and an integrated value of current inputted to the electric power source 10, respectively. The impedance measuring unit 66 uses the voltage sensor 150 and the current sensor 152 to measure impedance (internal resistance). The state-of-health estimating unit 70 obtains a state of health (SOH) of the electric power source 10, based on an integrated value of current outputted from the electric power source 10, an integrated value of current inputted to the electric power source 10, impedance, and temperature measured by use of the temperature sensor 154, by performing a well-known method.

The control unit 50 obtains, by the mapping 72, a full charge capacity of the electric power source 10 from the state of health (SOH) of the electric power source 10. By using the integrated consumed capacity of the electric power source 10 derived by the integrated consumed capacity derivation unit 68 and the full charge capacity, a state of charge or a remaining capacity of the electric power source 10 that is required for driving the load 121R for a amount corresponding to the above-explained predetermined number of times is derived. An open circuit voltage ($V_{th1}$) to be used as the primary first threshold value is derived from the required state of charge or the required remaining capacity of the electric power source 10 that is derived by using the mapping 74 of the state of charge (SOC) of the electric power source 10 and the open circuit voltage of the electric power source 10.

It has been known that the mapping 74 with respect to the state of charge (SOC) of the electric power source 10 and the open circuit voltage of the electric power source 10 is dependent on the state of deterioration of the electric power source 10; so that it is preferable that plural mappings 74 corresponding to states of deterioration of the electric power source 10 be stored in the memory 58 in advance.

As explained above, in the SOC-OCV method that uses a characteristic that the state of charge and the voltage of the electric power source have one-to-one relationship between them, a state of charge can be estimated from a voltage of the electric power source, that is obtained when it is used, by using mapping of a state of charge corresponding to the type of an electric power source and a voltage of the electric power source in advance. In this regard, it is preferable that the voltage of the electric power source be an open circuit voltage.

In this example, the algorithm that derives an open circuit voltage as the primary first threshold value has been explained in detail. Instead of the above, in the case that a state of charge (SOC) or a remaining capacity of the electric power source 10 is used as a value representing the remaining amount of the electric power source 10, "a state of charge or a remaining capacity of the electric power source 10 that is required for driving the load 121R for a amount corresponding to the predetermined number of times" derived in the stage before the mapping 74 shown in FIG. 13 may be used as the primary first threshold value. Alternatively, the mapping 74 and/or the full charge capacity and "a state of charge or a remaining capacity of the electric power source 10 that is required for driving the load 121R for a amount corresponding to the predetermined number of times," that is derived by use of the open circuit voltage derived by the mapping 74, may be used as the primary first threshold value.

Further, although the algorithm for deriving the primary first threshold value in the present example is different from that in the previously explained example, the threshold value changing process can be performed according to the flow chart shown in FIG. 11.

(The Other Example of the Threshold Value Changing Process)

Figure 14:
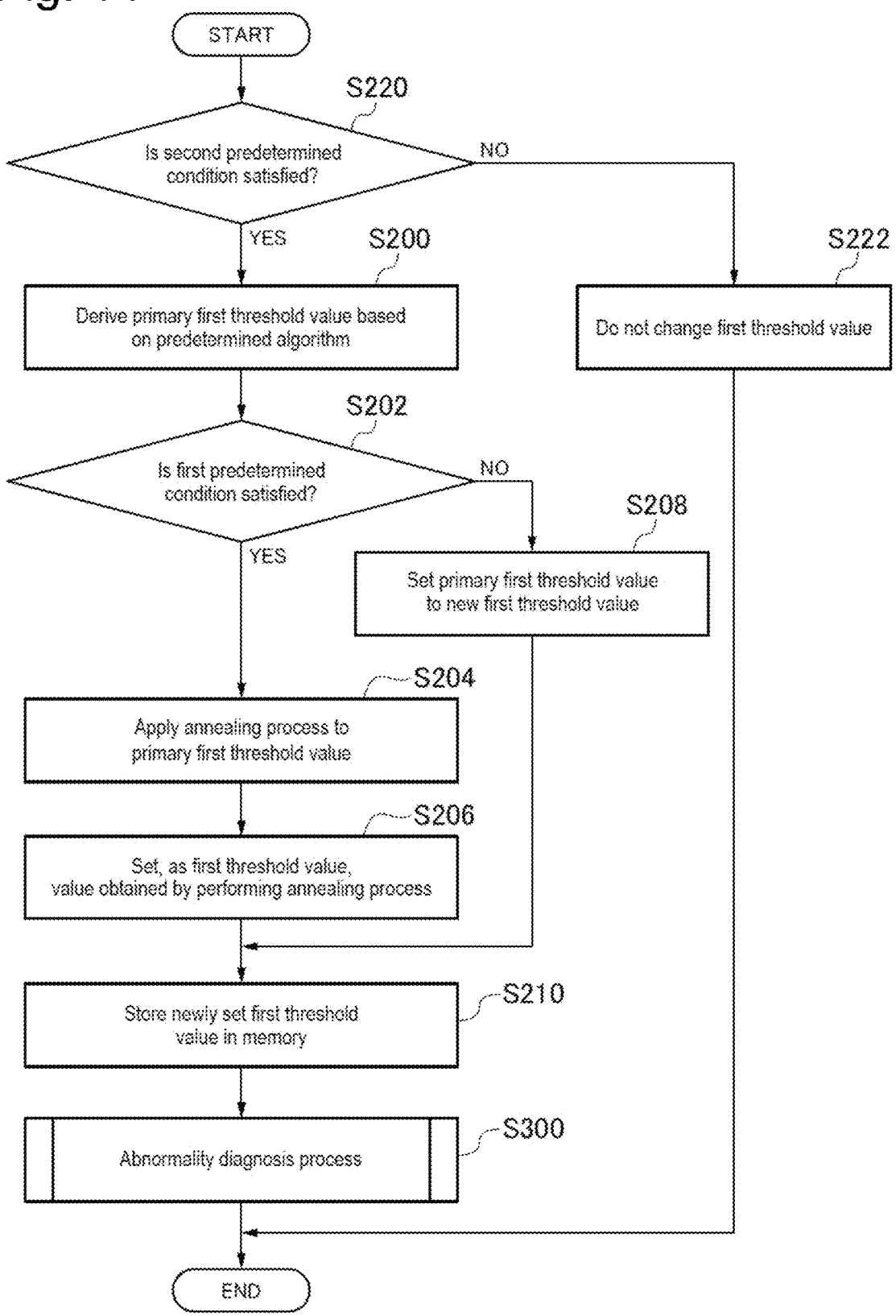
FIG. 14 is a flow chart showing the other example of a threshold value changing process.
Figure 15:
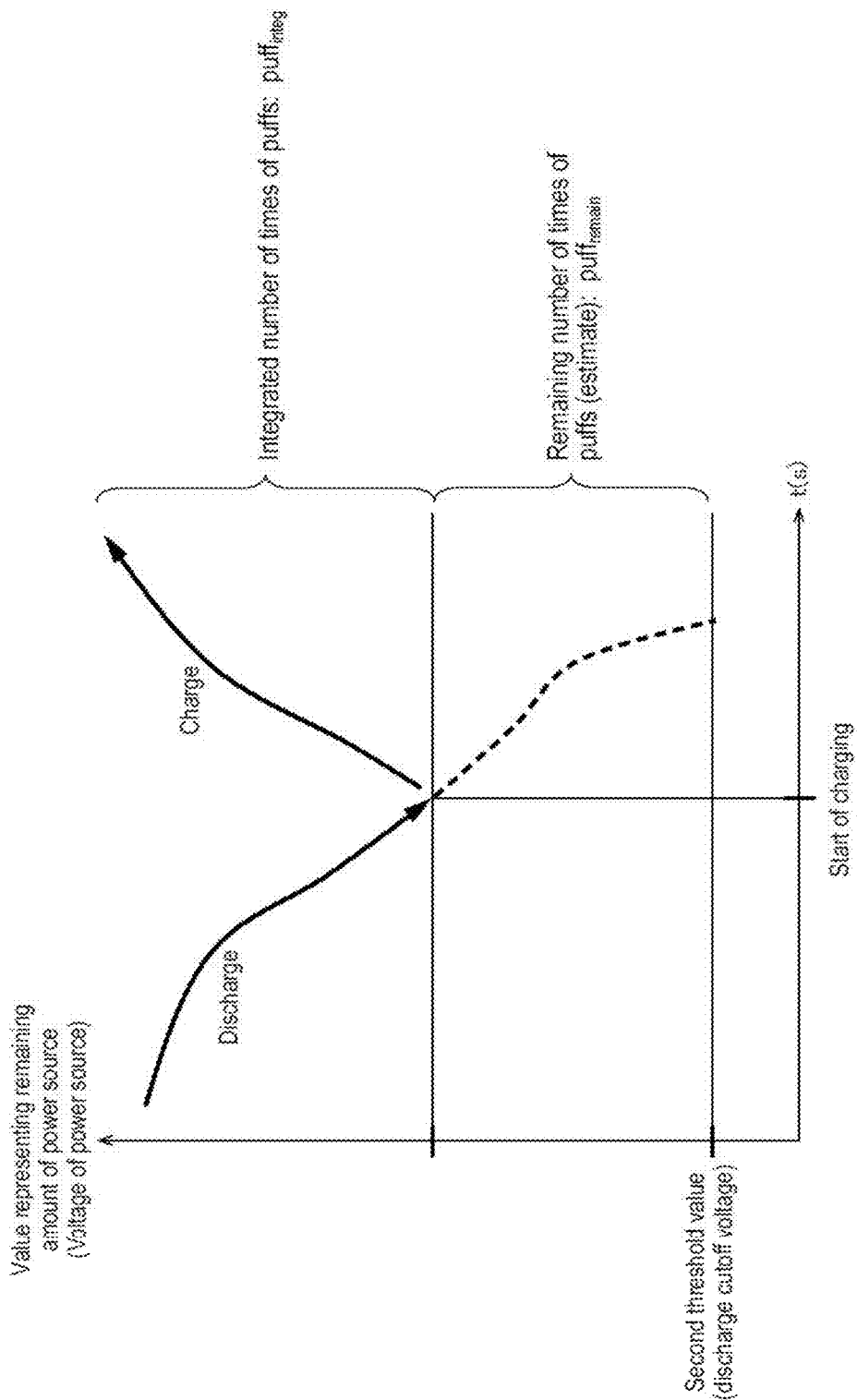
FIG. 15 is a graph showing behavior of the voltage value of an electric power source, in the case that charging is started before the voltage of the electric power source reaches a discharge cutoff voltage.

The other example of the threshold value changing process will be explained. FIG. 14 is an example of a flow chart of a threshold value changing process. In the case that charging of the electric power source 10 is performed before the value representing the remaining amount of the electric power source 10 becomes a value less than the second threshold value, it is preferable that the control unit 50 perform the threshold value changing process S104. Note that FIG. 15 shows states of the voltage value of the electric power source, in the case that charging is started before the voltage of the electric power source 10 reaches the second threshold value, for example, the discharge cutoff voltage.

In the threshold value changing process relating to this example, if a second predetermined condition is not satisfied, it is preferable that the first threshold value be unchanged and the threshold value changing process be terminated (steps S220 and S222).

In an embodiment, the second predetermined condition is a condition that the amount of operation of the load 121R or the amount of inhalation components generated by the load 121R, at or before the time when charging of the electric power source 10 is started, is equal to or greater than a reference amount. That is, in the case that the amount of operation of the load 121R or the amount of inhalation components generated by the load 121R, at or before the time when charging of the electric power source 10 is started, is less than the reference amount, the first threshold value is not changed. In this regard, the amount of operation of the load 121R or the amount of inhalation components generated by the load 121R is calculated from the point in time that charging was performed last time.

In the other embodiment, the second predetermined condition is a condition that a value obtained by the control unit 50 at or before the time when charging of the electric power source 10 is started is less than the first threshold value. That is, in the case that the value representing the remaining amount of the electric power source 10, that is obtained by the control unit 50 at or before the time when charging of the electric power source 10 is started, is equal to or greater than the first threshold value, the first threshold value is not changed. More specifically, if the value representing the remaining amount of the electric power source 10 is equal to or greater than the first threshold value, it is preferable that the first threshold value be unchanged even if the electric power source 10 is charged.

With respect to the above-explained second predetermined condition, it means the condition that the remaining amount of the electric power source 10 is large, i.e., the number of times of puff actions is small. Thus, it is considered that the first threshold value that separates the normal use mode and the charge requesting mode from one another has been set and maintained to be a relatively appropriate value, even if it is not changed.

In a further different embodiment, the second predetermined condition is a condition that leaving time, that is a period of time during that electric power is not supplied to the load 121R, is less than predetermined time. That is, in the case that the leaving time, that is a period of time during that electric power is not supplied to the load 121R, is equal to or greater than the predetermined time, the first threshold value is not changed. The leaving time can be measured by the above-explained timer 54.

If the leaving time becomes equal to or longer than the predetermined time, notable voltage drop due to self-discharge occurs. Thus, accuracy of the value of the primary first threshold value, that is derived by the threshold value changing process, more specifically, by a predetermined algorithm, may decrease. In the case that the first threshold value is changed by use of such a primary first threshold value, the first threshold value that separates the normal use mode and the charge requesting mode from one another may deviate from an appropriate value. Thus, in the above-explained case wherein notable voltage drop due to self-discharge occurs, it is preferable that the first threshold value be unchanged.

In the threshold value changing process, in the case that the second predetermined condition is satisfied, the primary first threshold value is derived based on the predetermined algorithm (step S200). In this example, the first threshold value is set based on a value that is larger than the second threshold value by a amount corresponding to the amount of voltage drop of the electric power source 10 when the load 121R has been driven for a amount corresponding to the predetermined number of times. In this regard, the amount of voltage drop of the electric power source 10 when the load 121R has been driven for a amount corresponding to the predetermined number of times may be a value estimated by the control unit 50. That is, the amount of voltage drop of the electric power source 10 is estimated based on a value representing the remaining amount of the electric power source 10 that is obtained by the control unit 50 at or before the time when charging of the electric power source is started. That is, in this example, the first threshold value is changed so that a predetermined number of times of puff actions, roughly, are allowed in the charge requesting mode.

Specifically, the control unit 50 obtains, per puff action, a voltage of the electric power source 10 as a value representing the remaining amount of the electric power source 10. The control unit 50 can thereby obtain a voltage drop amount per puff $\Delta V(i)$. In this regard, "i" is an index representing the number of times of puff actions.

When the electric power source 10 has been charged, the control unit 50 obtains an average value $_\Delta V_{AVE}$ of the voltage drop amounts relating to puff actions. In this regard, the average value $_\Delta V_{AVE}$ of the voltage drop amounts relating to puff actions may be calculated over the number of times of puff actions that have been performed since charging of the electric power source 10 was performed last time.

Alternatively, the average value $_\Delta V_{AVE}$ of the voltage drop amounts relating to puff actions may be calculated over the number of times of puff actions that have been performed after the voltage of the electric power source 10 has decreased to a value below a predetermined value. In such a case, the predetermined value may be the presently set first threshold value. In such a case, if charging of the electric power source 10 is started before the voltage of the electric power source 10 decreases to a value below the first threshold value, the control unit 50 is not required to change the first threshold value.

The control unit 50 estimates, by using the average value $_\Delta V_{AVE}$ of the voltage drop amounts, a remaining number of times of puff actions at the time when charging is started. The remaining number of times of puff actions is an index that shows the number of times of puff actions that can be performed in relation to the remaining amount of the electric power source at the time when charging is started. The remaining number of times of puff actions can be estimated under supposition that the voltage of the electric power source 10 decreases linearly in relation to puff actions, for example. In such a case, the remaining number of times of puff actions ($puff_{remain}$) can be obtained by use of the following formula: $puff_{remain}=(V(N)-(\text{discharge cutoff voltage}))/_\Delta V_{AVE}$. In this regard, V(N) means a voltage of the electric power source 10 at the time when charging is started.

The control unit 50 may use the thus estimated remaining number of times of puff actions $puff_{remain}$, obtain, from the memory 58, the voltage ($OCV(N+puff_{remain}-N_{re})$) of the electric power source 10 obtained at timing that is, in terms of the number of times of puff actions, the predetermined number of times ($N_{re}$) before the sum of the number of times of puff actions measured since charging is performed (N) and the remaining number of times of puff actions ($puff_{remain}$), and set it as the primary first threshold value.

As explained above, if the first predetermined condition is not satisfied, the control unit 50 sets the primary first threshold value to a new first threshold value (steps S202 and S208). If the first predetermined condition is satisfied, the control unit 50 sets the first threshold value to a value obtained by applying the annealing process to the primary first threshold value (steps S202, S204, and S206). In this regard, the first predetermined condition may be a condition that the state of deterioration of the electric power supply 10 has not yet progressed beyond a predetermined judgment state, for example.

The predetermined number of times ($N_{re}$) is that explained above, and may be a preset fixed value, or a variable value that is settable by a user.

(A Further Different Example of the Predetermined Algorithm)

Figure 16:
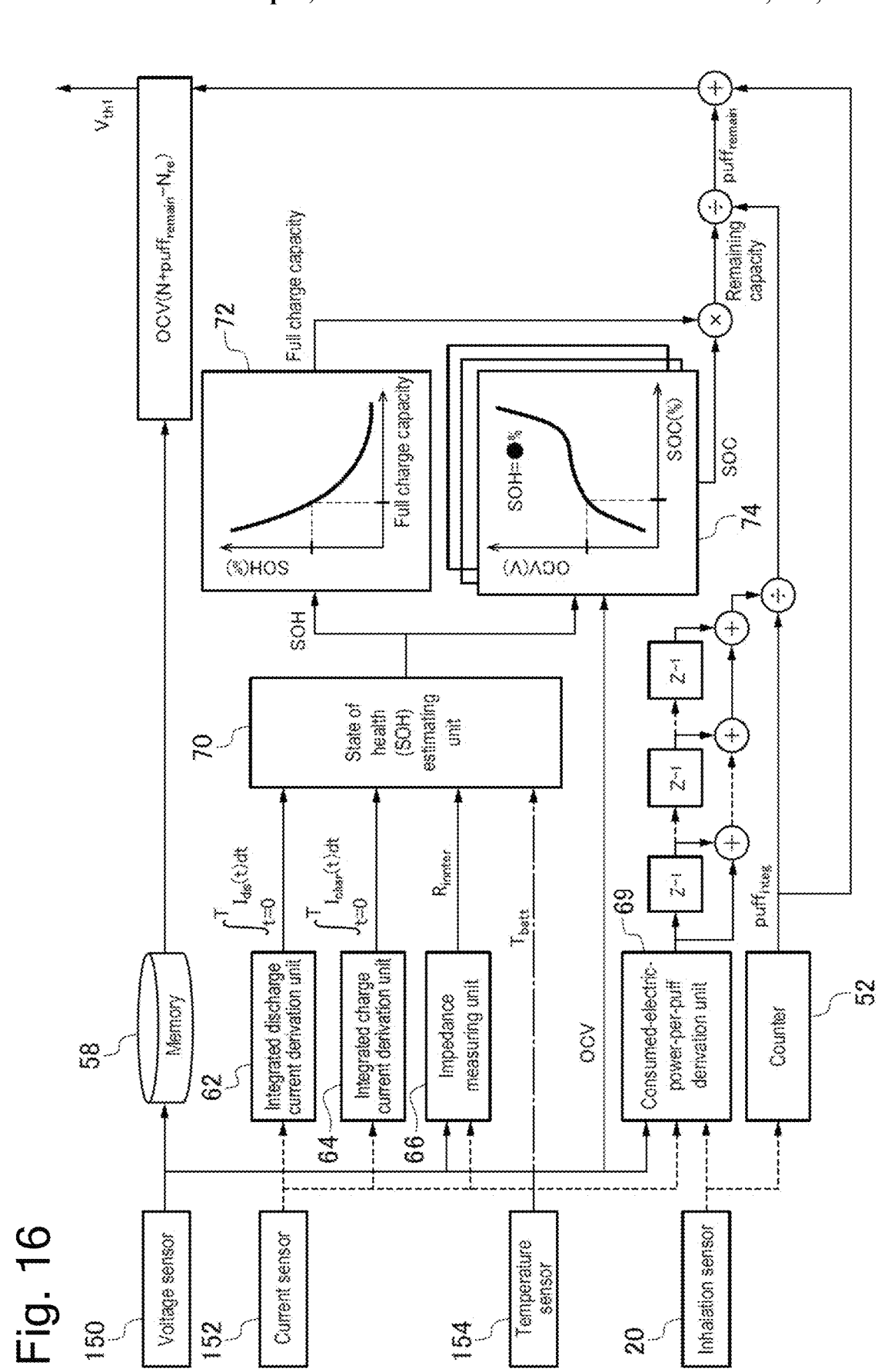
FIG. 16 is the other example of a block diagram of a control unit for implementing a predetermined algorithm.

Next, a further different example of the predetermined algorithm will be explained. FIG. 16 shows a block diagram of a control unit for implementing the predetermined algorithm relating to this example.

In the example shown in FIG. 16, the value representing the remaining amount of the electric power source 10 is determined by using a state of charge (SOC) or a remaining capacity of the electric power source 10. In this case, the second threshold value may be a state of charge or a remaining capacity of the electric power source when the voltage of the electric power source has become the discharge cutoff voltage. Also, in this case, in the flow chart shown in FIG. 7, the control unit 50 obtains, as a value representing the remaining amount of the electric power source 10, a state of charge or a remaining capacity of the electric power source 10. The obtained state of charge or the obtained remaining capacity is stored in the memory 58 every time a puff action is performed. Also, in the case that a state of charge (SOC) of the electric power source 10 is used as a value representing the remaining amount of the electric power source 10, the second threshold value in step S110 and the first threshold value in step S116 are made to be values that are appropriate for comparison with a state of charge (SOC), so that the dimension (unit) of each of the values is made to be (%). On the other hand, in the case that a remaining capacity of the electric power source 10 is used as a value representing the remaining amount of the electric power source 10, the first threshold value in step S110 and the second threshold value in step S116 are made to be values that are appropriate for comparison with a remaining capacity, so that the dimension (unit) of each of the values is made to be (Wh).

It is preferable that the predetermined algorithm relating to this example be performed when the state of charge of the electric power source 10 becomes equal to or less than a state of charge or a remaining capacity corresponding to the discharge cutoff voltage. In the algorithm, the first threshold value is changed based on a value that is larger than the second threshold value by a amount of drop of the state of charge or the remaining capacity of the electric power source 10 when the load 121R is operated for a amount corresponding to the predetermined number of times. The amount of drop of the state of charge or the remaining capacity of the electric power source 10 may be estimated based on a amount of drop of a state of charge or a remaining capacity of the electric power source 10 obtained by the control unit 50 at or before the time when charging of the electric power source 10 is started.

The state of charge (SOC) or the remaining capacity of the electric power source 10 can be estimated by a well-known SOC-OCV method, a current integration method (a coulomb count method), and so on, for example. FIG. 16 shows an example in which an SOC-OCV method is used. In the method, the control unit 50 comprises a state-of-health estimating unit 70 for estimating the state of deterioration of the electric power source 10. Further, the control unit 50 comprises an integrated discharge current derivation unit 62, an integrated charge current derivation unit 64, an impedance measuring unit 66, and a consumed-electric-power-per-puff derivation unit 69.

The integrated discharge current derivation unit 62 and the integrated charge current derivation unit 64 use the current sensor 152 to calculate an integrated value of current outputted from the electric power source 10 and an integrated value of current inputted to the electric power source 10, respectively. The impedance measuring unit 66 uses the voltage sensor 150 and the current sensor 152 to measure impedance (internal resistance). The state-of-health estimating unit 70 obtains a state of health (SOH) of the electric power source 10, based on an integrated value of current outputted from the electric power source 10, an integrated value of current inputted to the electric power source 10, impedance, and temperature measured by use of the temperature sensor 154, by performing a well-known method.

The control unit 50 obtains a full charge capacity of the electric power source 10, from the state of health (SOH) of the electric power source 10 and by use of the mapping 72. Also, the control unit 50 derives a state of charge (%), from a voltage value of the electric power source 10 at the time when charging is started, by using an appropriate mapping 74 based on a state of health (SOH) of the electric power source 10. The control unit 50 can estimate the remaining amount of the electric power source 10 at the time when charging is started, by multiplying the obtained full charge capacity and the state of health (SOH) of the electric power source 10 with each another.

Further, the control unit 50 derives an estimate value of the amount of electric power consumption required for a single puff action, by dividing, by the number of times of puff actions, an accumulated value of amounts of electric power consumption for respective puff actions derived by the consumed-electric-power-per-puff derivation unit 69. The control unit 50 can estimate a remaining number of times of puffs ($puff_{remain}$), by dividing the remaining amount of the electric power source 10 at the time when charging is started by the estimate value of the amount of electric power consumption required for a single puff action.

The control unit 50 may use the thus estimated remaining number of times of puff actions $puff_{remain}$, obtain, from the memory 58, the voltage ($OCV(N+puff_{remain}-N_{re})$) of the electric power source 10 obtained at timing that is, in terms of the number of times of puff actions, the predetermined number of times ($N_{re}$) before the sum of the number of times of puff actions measured since charging is performed (N) and the remaining number of times of puff action ($puff_{remain}$), and set it as the primary first threshold value.

As explained above, if the first predetermined condition is not satisfied, the control unit 50 sets the primary first threshold value to a new first threshold value (steps S202 and S208). If the first predetermined condition is satisfied, the control unit 50 sets the first threshold value to a value obtained by applying the annealing process to the primary first threshold value (steps S202, S204, and S206). In this regard, the first predetermined condition may be a condition that the state of deterioration of the electric power supply 10 has not yet progressed beyond a predetermined judgment state, for example.

The predetermined number of times ($N_{re}$) is that explained above, and may be a preset fixed value, or a variable value that is settable by a user.

In this example, the algorithm that derives an open circuit voltage as the primary first threshold value has been explained in detail. Instead of the above, in the case that a state of charge (SOC) or a remaining capacity of the electric power source 10 is used as a value representing the remaining amount of the electric power source 10, "a state of charge or a remaining capacity of the electric power source 10 that is required for driving the load 121R for a amount corresponding to the predetermined number of times" derived in the stage before the mapping 74 shown in FIG. 16 may be used as the primary first threshold value. Alternatively, the mapping 74 and/or the full charge capacity and "a state of charge or a remaining capacity of the electric power source 10 that is required for driving the load 121R for a amount corresponding to the predetermined number of times," that is derived by use of the open circuit voltage derived by the mapping 74, may be used as the primary first threshold value.

Further, although the algorithm for deriving the primary first threshold value in the present example is different from that in the previously explained example, the threshold value changing process can be performed according to the flow chart shown in FIG. 14, for example.

(Control by an External Processor)

In the above example, the control unit 50 performs all parts of the process for changing the first threshold value, by using a value representing the remaining amount of the electric power source 10, according to the predetermined algorithm. Alternatively, at least a part of the process may be performed by a processor 250 in an external electric power source, for example, a processor in the charger 200.

For example, the inhalation component generation device 100 may be communicable with the processor 250 in the external electric power source which can estimate the remaining amount of the electric power source 10 at or before the time when charging is started. The processor 250 can estimate the remaining amount of the electric power source 10 at or before the time when charging of the electric power source 10 is started, and a value representing the estimated remaining amount of the electric power source 10 may be sent to the inhalation component generation device 100.

The processor 250 can estimate the remaining amount of the electric power source 10, based on a value representing the amount of electric power discharged from the electric power source 10 to the external electric power source 210, and a value representing the amount of electric power charged to the electric power source 10 from the external electric power source 210. These amounts of electric power can be derived by using the current sensor 230 and the voltage sensor 240.

Estimating of the remaining amount of the electric power source 10 by the processor 250 may be performed by using an arbitrary well-known method. For example, the remaining amount of the electric power source 10 can be estimated by use of a ratio between the amount of discharged electric power of the electric power source 10 discharged until the discharge cutoff voltage and the amount of charged electric power of the electric power source 10 charged from the discharge cutoff voltage to the full charge voltage, when the electric power source is connected to the charger 200. In such a case, derivation of the amount of discharged electric power and the amount of charged electric power can be made, for example, by charging the electric power source 10 to have the full charge voltage after discharging it to the discharge cutoff voltage.

In the case that the remaining amount of the electric power source 10 is estimated by the processor 250, the control unit 50 may change the first threshold value based on the remaining amount of the electric power source 10 obtained from the processor 250. Specifically, the control unit 50 can derive a primary first threshold value by using the remaining amount of the electric power source 10 obtained from the processor 250 and applying one of the above-explained predetermined algorithms.

(An Annealing Process)

Figure 17:
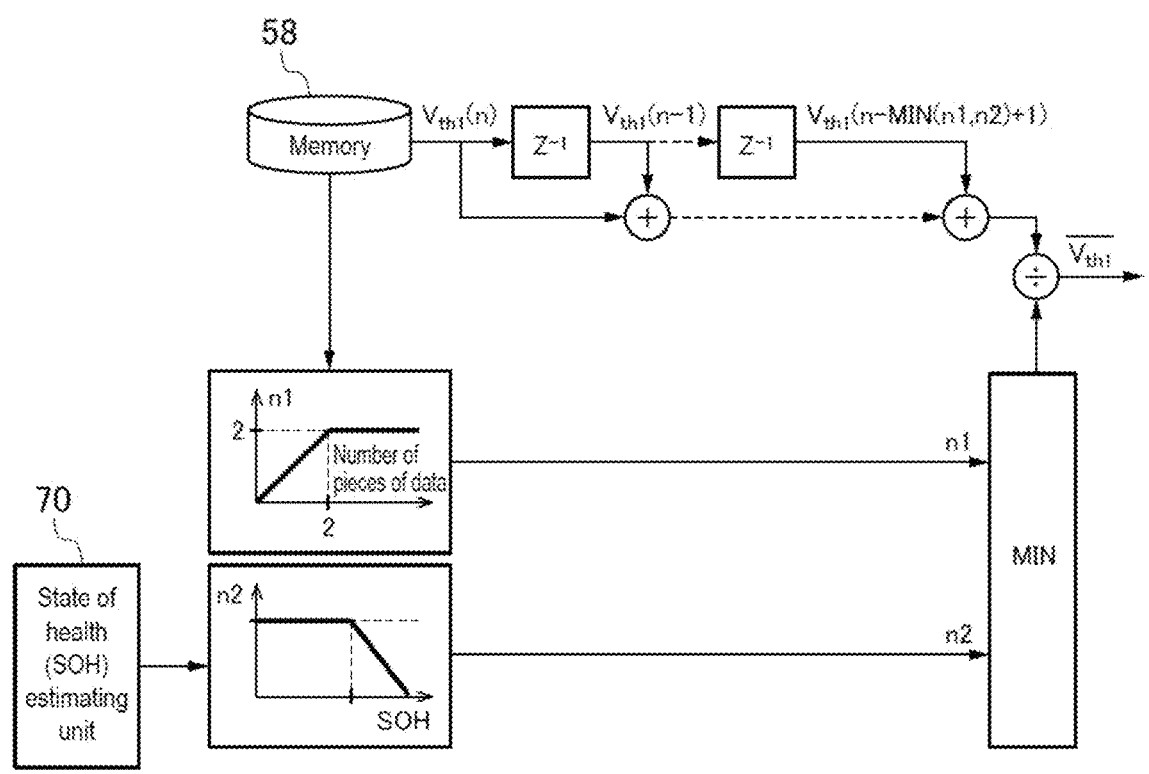
FIG. 17 is an example of a block diagram of a control unit for implementing an annealing process.

FIG. 17 is an example of a block diagram of a control unit for implementing an annealing process. The annealing process may be a process for obtaining a moving average of the most recent predetermined number of first threshold values in previously changed plural first threshold values, for example. That is, the annealing process is an average value of a predetermined number of first threshold values that are extracted, from the newest in time series, from the plural first threshold values ($V_{th1}$) stored in the memory.

As explained above, the predetermined algorithm derives a primary first threshold value based on a value of a voltage of the electric power source 10. However, the value of the voltage of the electric power source 10 may include change due to various environments such as a temperature condition and so on and errors, so that if the primary first threshold value is set to a first threshold value in a simple manner, there may be a case that the first threshold value changes greatly from a previous first threshold value. By setting a new first threshold value to a value obtained by applying the annealing process to the primary first threshold value, change due to various environments such as a temperature condition and so on and errors can be reduced. In addition, the influence of minor differences between the ways of inhalation relating to respective inhalation actions of a user, and product errors and aging of the inhalation component generation device 100, on the new first threshold value, can be reduced. Further, by suppressing occurrence of large change of the newly set first threshold value, an unnatural feel sensed by a user can be suppressed.

In an example, the strength of the annealing process may be changed based on the number of previously changed first threshold values, specifically, the number of first threshold values stored in the memory 58. For example, if the number of first threshold values already stored in the memory 58 is 0, the control unit 50 sets, as a first threshold value, a primary first threshold value derived by the predetermined algorithm, without performing the annealing process. That is, in the above case, the number of first threshold values (n1) used in the annealing process is 0.

On the other hand, if the number of first threshold values already stored in the memory 58 is 1, the control unit 50 may set, as a first threshold value, an average value of the first threshold value stored in the memory 58 and the primary first threshold value derived by the predetermined algorithm. That is, in the above case, the number of first threshold values (n1) used in the annealing process is 1.

Further, if the number of first threshold values already stored in the memory 58 is 2 or more than 2, the control unit 50 may set, as a first threshold value, an average value of two first threshold values stored in the memory 58 and the primary first threshold value derived by the predetermined algorithm. That is, in the above case, the number of first threshold values (n1) used in the annealing process is 2.

In this manner, by changing, according to the number of first threshold values stored in the memory 58, the number of values that are used for calculating a moving average, the strength of the annealing process can be set appropriately. As a result, occurrence of the case that the first threshold value cannot be changed appropriately since the strength of the annealing process is too high can be prevented, and occurrence of the case that the process does not function since the strength of the annealing process is too low can be prevented.

Further, the strength of the annealing process may be changed based on a state of health (SOH) of the electric power source 10. Specifically, it is preferable that the strength of the annealing process be made to be weaken as the state of deterioration progresses. Specifically, the number of first threshold values (n2) used in the annealing process may be reduced as the state of deterioration progresses. More preferably, the number of first threshold values used in the annealing process may be a smaller one of the number (n1) corresponding to the number of first threshold values stored in the memory 58 and the number (n2) obtained based on the state of health (SOH) of the electric power source 10 (refer to FIG. 17).

For example, if the state of health (SOH) of the electric power source 10 is equal to or lower than a first judgment state, the control unit 50 may set a first threshold value to an average value of two first threshold values stored in the memory 58 and the primary first threshold value derived by the predetermined algorithm. On the other hand, if the number of first threshold values stored in the memory 58 is less than 2, the number of first threshold values to be used in the annealing process may be reduced according to the number of threshold values stored in the memory 58. Similarly, if no first threshold value is stored in the memory 58, it is not necessary to perform the annealing process.

Further, in the case that the state of health (SOH) of the electric power source 10 has progressed beyond the first judgment state and becomes a state equal to or lower than a second judgment state, the control unit 50 may set a first threshold value to an average value of a single first threshold value stored in the memory 58 and the primary first threshold value derived by the predetermined algorithm. In this regard, if no first threshold value is stored in the memory 58, it is not necessary to perform the annealing process.

Further, in the case that the state of health (SOH) of the electric power source 10 has progressed beyond the second judgment state, it is preferable that the control unit 50 set a first threshold value to the primary first threshold value derived by the predetermined algorithm (steps S202 and S208).

As deterioration of the electric power source 10 progresses, the value representing the remaining amount of the electric power source 10, for example, the value of the voltage of the electric power source 10, the state of charge of the electric power source 10, or the remaining capacity of the electric power source 10, may change steeply. In such a case, it becomes possible to set, in the threshold value changing process, the first threshold value to a value that reflects the state of health (SOH) of the electric power source 10, by weakening the strength of the annealing process or making the annealing process not to be performed.

In the annealing process, it is preferable that a first threshold value, that is obtained after attaching the load 121R to the connection part 120*t*, only be used by the control unit 50. Further, the control unit 50 may make at least part, preferably, all, of first threshold values stored in the memory 58 to be unusable, or may delete it/them. As a result, it becomes possible to prevent the first threshold values, that are obtained before attaching the load 121R to the connection part 120*t*, from being used in the annealing process.

Note that, in this example, as an annealing process with respect to a primary first threshold value, a process for calculating a moving average of a primary first threshold value and a first threshold value(s) stored in the memory 58 has explained in detail. Alternatively, it may be possible to use an annealing process in which a least squares method is applied to a data group comprising plural first threshold values stored in the memory 58, or to a data group comprising the plural first threshold values and a primary first threshold value. As a further alternative, it may be possible to perform a weighted moving average process or an exponential moving average process in an annealing process, wherein heavier weight is given to a newer first threshold value stored in the memory 58.

Also, in this example, the algorithm that does not store a primary first threshold value derived in step S200 in each of FIGS. 11 and 14 in the memory 58, and treats the primary first threshold value as a temporary variable value in a control flow has explained in detail. In place of the above embodiment, it is possible to store a primary first threshold value derived in step S200 in each of FIGS. 11 and 14 in the memory 58 before performing the annealing process. That is, in FIG. 17, until the annealing process is performed, the newest data $V_{th1}(n)$ stored in the memory 58 is a primary first threshold value derived in step S200 in each of FIGS. 11 and 14. Thus, when the strength of the annealing process is to be set, as explained above, based on the first threshold value stored in the memory 58 or the state of health (SOH) of the electric power source 10, at least one piece of data has been stored in the memory 58. In this case, in the annealing process, it is necessary to increase, with respect to the range of all first threshold values stored in the memory 58, the number (n1) corresponding to the number of first threshold values stored in the memory 58 by 1. Similarly, it is necessary to increase, with respect to the range of all states of health (SOHs) of the electric power source 10, the number (n2) obtained based on the states of health (SOHs) of the electric power source 10 by 1. Further, it should be reminded that the primary first threshold value $V_{th1}(n)$ stored in the memory 58 should be overwritten by a new first threshold value obtained by performing the annealing process.

Also, in this example, an annealing process in the case that voltages of the electric power source 10 are used as a value representing a remaining amount of the electric power source 10, a primary first threshold value, and a first threshold value has explained. Alternatively, states of charge (SOCs) or remaining capacities of the electric power source 10 may be used as a value representing a remaining amount of the electric power source 10, a primary first threshold value, and a first threshold value.

(Measures Applied to Cope with Long Term Leaving)

If the above-explained threshold value changing process is performed after the electric power source 10 has been left for a long time, accuracy of the above-explained algorithm may be lowered due to self-discharge. Thus, it is preferable that the control unit 50 correct, according to the leaving time, the first threshold value that is changed based on an operation requesting signal. In this regard, the leaving time is that determined based on a period of time during that no electric power is supplied to the load 121R, and can be measured by the timer 54, as explained above.

Figure 18:
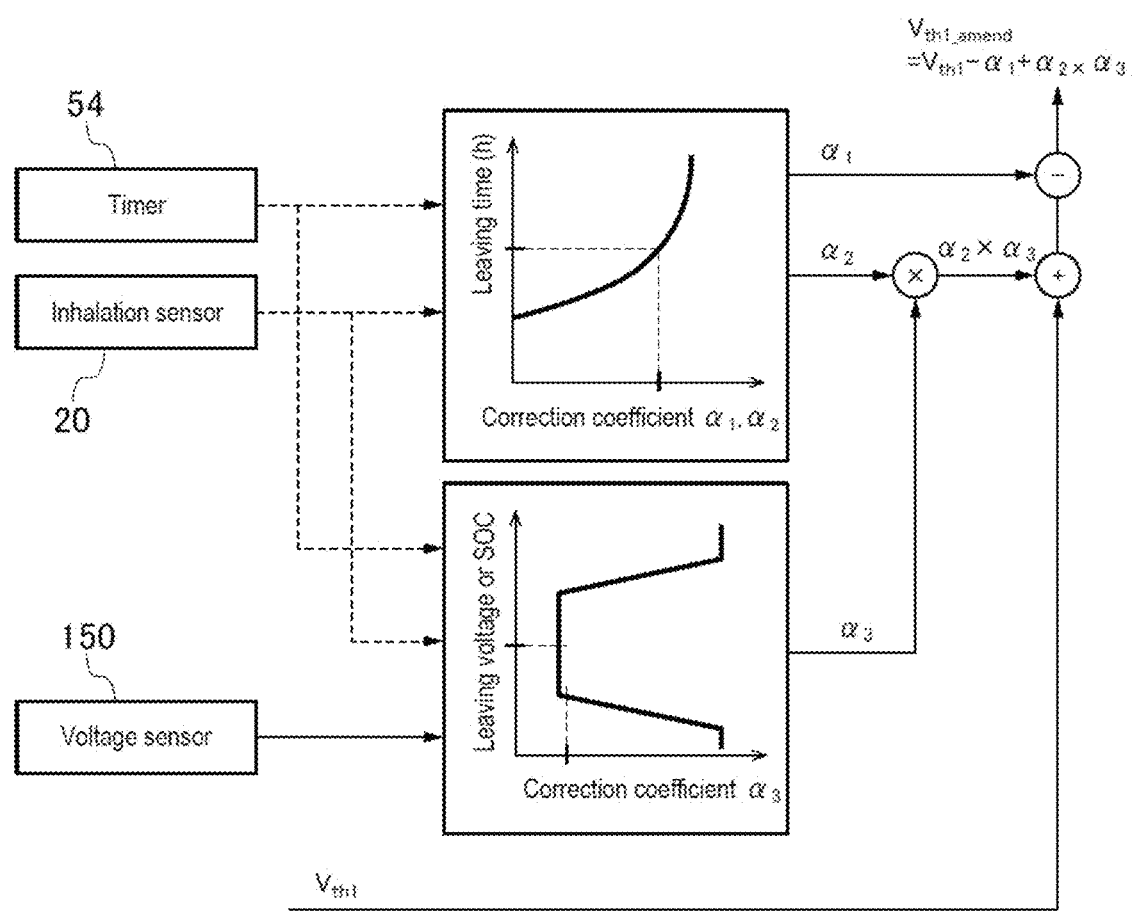
FIG. 18 is an example of a block diagram of a control unit for performing correction of a first threshold value, in the case that a threshold value changing process is performed after long time leaving.

FIG. 18 is an example of a block diagram of a control unit for performing correction of a first threshold value, in the case that a threshold value changing process is performed after long term leaving. In this example, the control unit 50 corrects a primary first threshold value ($V_{th1}$) derived by the predetermined algorithm, by using the following formula:
$V_{th1\_amend} = V_{th1} - \alpha 1 + \alpha 2 * \alpha 3$ In the above, $V_{th1\_amend}$ is a primary first threshold value after correction. $V_{th1}$ is a primary first threshold value before correction, that is, a primary first threshold value derived by the above-explained predetermined algorithm. α1, α2, and α3 are correction coefficients, respectively.

The correction coefficient α1 is a coefficient for compensating for natural dropping of the voltage of the electric power source 10 relating to leaving of the electric power source 10. According to the above-explained predetermined algorithm, if correction corresponding to the leaving time is not made, there may be a case that the primary first threshold value is set to a value that is higher by a value corresponding to voltage drop due to self-discharge. Thus, the correction coefficient α1 may be set for cancelling out the voltage drop due to self-discharge. That is, it is preferable that the control unit 50 perform correction to make the primary first threshold value to be a smaller value corresponding to the leaving time.

The correction coefficients α2 and α3 are coefficients for compensating for capacity deterioration (in other words, lowering of a full charge capacity) of the electric power source 10 relating to leaving of the electric power source 10. In general, it has been known that deterioration of the electric power source 10 progresses and a full charge capacity decreases, if it is left for a long period of time. Further, the degree of decrease is dependent on the remaining amount of the electric power source 10 when it is to be left. According to the above-explained predetermined algorithm, if correction corresponding to the leaving time is not made, there may be a case that the primary first threshold value is set to a value that is lower by a value corresponding to the decrease in the full charge capacity. Thus, it is preferable that correction based on the correction coefficients α2 and α3 be performed to take decrease in the full charge capacity relating to long term leaving into consideration.

The correction coefficient α3 is a value corresponding to a remaining amount of the electric power source 10 when the load 121R is operated or inhalation components are generated. More specifically, the correction coefficient α3 is a value corresponding to a remaining amount of the electric power source 10 when the load 121R is operated after the electric power source 10 has been left. As explained above, decrease in the full charge capacity of the electric power source 10 relating to long term leaving is dependent on the remaining amount the electric power source when it was left. Especially, a full charge capacity of the electric power source 10 tends to decrease easily, if long term leaving of the electric power source 10 is started when the remaining amount is close to a amount corresponding to a full charge voltage or a discharge cutoff voltage. In view of the above matter, it is preferable that a primary first threshold value be corrected to have a larger value, as the remaining amount the electric power source 10, at the time of discharging, is closer to a full charge voltage or a discharge cutoff voltage.

Further, decrease in electric power storage capacity (≈ a possible number of times of puff actions) relating to leaving of the electric power source 10 is affected by the length of the leaving time. Thus, the control unit 50 may correct the primary first threshold value, by adding, to the primary first threshold value, the product of the correction coefficient α2 and the correction coefficient α3 that are based on the remaining amount at the time of starting of leaving of the electric power source 10.

It should be reminded that relationship between the correction coefficients α1 and α1 and the leaving time is determined by the type (design) of the electric power source 10 that is used. Similarly, relationship between the correction coefficient α3 and the discharge voltage, the state of charge, or the remaining capacity is determined by the type (design) of the electric power source 10 that is used. Thus, the correction coefficients a1, a2, and a3 can be derived by performing an experiment in advance, with respect to the electric power source 10 that is to be used.

The control unit 50 sets a first threshold value to the thus corrected value. Further, as explained above, it is possible to set a first threshold value to a value that is obtained by applying an annealing process to the thus corrected value.

Also, in this example, an annealing process in the case that voltages of the electric power source 10 are used as a value representing a remaining amount of the electric power source 10, a primary first threshold value, and a first threshold value has explained. Alternatively, states of charge (SOCs) or remaining capacities of the electric power source 10 may be used as a value representing a remaining amount of the electric power source 10, a primary first threshold value, and a first threshold value.

(An Abnormality Judging Process)

Figure 19:
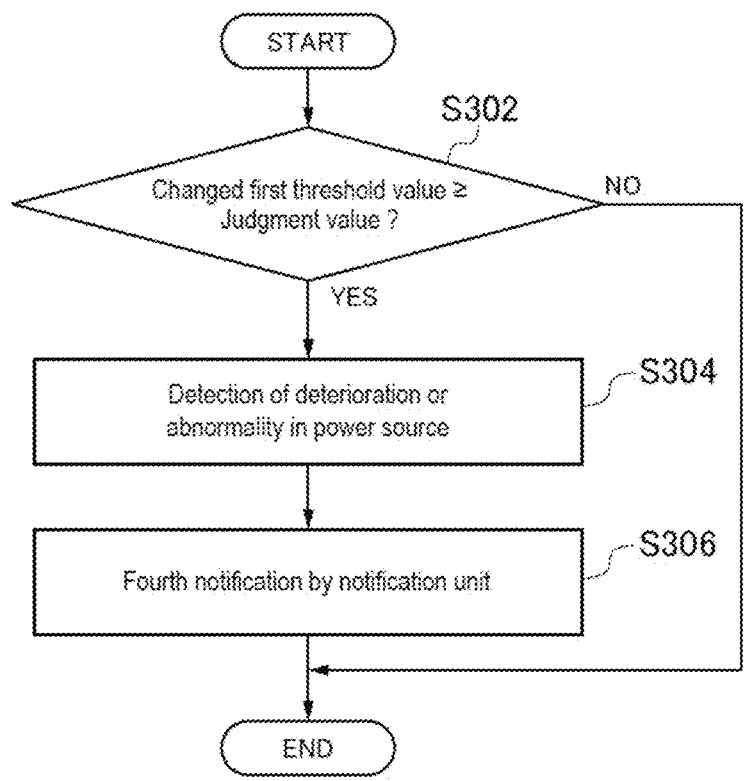
FIG. 19 is a flow chart showing an example of an abnormality judging process.

FIG. 19 is a flow chart showing an example of an abnormality judging process. The control unit 50 detects deterioration or abnormality in the electric power source 10, if the changed first threshold value is equal to or greater than a predetermined judgment value (step S302).

In the deteriorated electric power source 10, the value representing the remaining amount of the electric power source 10 steeply reduces in relation to the number of times of puff actions. Thus, if it is attempted to change the first threshold value based on a value that allows operation of the load 121R or generation of inhalation components corresponding to the predetermined number of times, the first threshold value becomes larger as deterioration of the electric power source 10 progresses further. Accordingly, it is possible to consider that deterioration of the electric power source 10 or abnormality in the electric power source 10 has occurred, if the changed first threshold value is equal to or greater than the predetermined judgment value.

In this regard, the predetermined judgment value may be set to a predetermined value corresponding to a state wherein it can be considered that deterioration of the electric power source 10 or abnormality in the electric power source 10 has occurred. In the case that the value representing the remaining amount of the electric power source 10 is a voltage of the electric power source, and that a lithium-ion secondary battery is used as the electric power source 10, the predetermined judgment value may be that in the range of 3.7-3.9 V, for example.

The control unit 50 controls the notification unit 40 to perform a fourth notification, when deterioration of the electric power source 10 or abnormality in the electric power source 10 is detected (step S306). It is preferable that the fourth notification be different from the above-explained first notification, second notification, and third notification. In the case that the notification unit 40 is a light emitting element, the emitted-light color and the light emitting pattern of the light emitting element with respect to the fourth notification may be different from the emitted-light color and the light emitting pattern of the light emitting element with respect to each of the first notification, the second notification, and the third notification.

The control unit 50 may stop, when it has detected abnormality, the whole operation of the inhalation component generation device 100.

Other Embodiments

Although the present invention has been explained by use of the above embodiments, the descriptions and figures that are components of part of the disclosure should not be interpreted as those used for limiting the present invention. From the disclosure, various alternative embodiments, examples, and operation techniques would become apparent to a person skilled in the art.

For example, regarding the embodiments explained in relation to the above embodiments, an embodiment can be combined with and/or replaced by the other embodiment(s), where possible.

Further, it should be reminded that a computer program(s) which configures an inhalation component generation device to perform the above-explained various methods, that are performed by the control unit 50, is(are) included in the scope of the present invention.

The invention claimed is:

1. An inhalation component generation device comprising:
   a load configured to vaporize or atomize an inhalation component source by electric power from an electric power source;
   a user interface; and
   circuitry configured to
      obtain a value representing a remaining amount of the electric power source, obtain an operation requesting signal to the load, and generate an instruction for operating the load;
      cause the user interface to perform a first notification in a case that the value representing the remaining amount of the electric power source is equal to or greater than a first threshold value;
      cause the user interface to perform a second notification in a case that the value representing the remaining amount of the electric power source is less than the first threshold value and equal to or greater than a second threshold value that is less than the first threshold value; and
      cause the user interface to perform a third notification in a case that the value representing the remaining amount of the electric power source is less than the second threshold value, wherein
   the first notification, the second notification, and the third notification are different from each other, and
   the first threshold value is a variable value.

2. The inhalation component generation device according to claim 1, wherein
   the user interface comprises a light emitting element,
   the first notification comprises a first light emission color by the light emitting element,
   the second notification comprises a second light emission color by the light emitting element,
   the third notification comprises a third light emission color by the light emitting element, and
   the first light emission color, the second light emission color, and the third light emission color are different from each other.

3. The inhalation component generation device according to claim 2, wherein
   the first light emission color includes a cold color,
   the third light emission color includes a warm color, and
   the second light emission color includes an intermediate color that is between the first light emission color and third light emission color in a hue circle.

4. The inhalation component generation device according to claim 2, wherein
   the distance between a complementary color of the first light emission color and the third light emission color on the hue circle is shorter than the distance between the complementary color of the first light emission color and the second light emission color on the hue circle.

5. The inhalation component generation device according to claim 2, wherein
   the distance between a complementary color of the third light emission color and the first light emission color on the hue circle is shorter than the distance between the complementary color of the third light emission color and the second light emission color on the hue circle.

6. The inhalation component generation device according to claim 2, wherein a wavelength corresponding to the second light emission color is closer to a wavelength corresponding to the first light emission color than a wavelength corresponding to the third light emission color.

7. The inhalation component generation device according to claim 2, comprising:
one end having an inhalation port for inhaling the inhalation component and another end opposite to the inhalation port, wherein
the light emitting element is arranged across the another end and a part of a side face extending between the one end and the another end.

8. The inhalation component generation device according to claim 7, wherein
the length from the one end to the another end is equal to or greater than 58 mm and equal to or less than 135 mm.

9. The inhalation component generation device according to claim 8, wherein
the length from the one end to the another end is equal to or greater than 100 mm and equal to or less than 135 mm.

10. The inhalation component generation device according to claim comprising:
one end having an inhalation port for inhaling the inhalation component and another end opposite to the inhalation port, wherein
the light emitting element is arranged at a side face which extends between the one end and the another end.

11. The inhalation component generation device according to claim 2, wherein
the load is configured to generate the inhalation component from the inhalation component source in the case that the value representing the remaining amount of the electric power source is equal to or greater than the second threshold value, and
the light emitting pattern of the light emitting element for the first notification is the same as that for the second notification.

12. The inhalation component generation device according to claim 1, wherein
the load is configured to generate the inhalation component from the inhalation component source, in a case that the value representing the remaining amount of the electric power source is equal to or greater than the second threshold value, and
the circuitry is configured to control the periods of the first notification and the second notification performed by the user interface to vary, according to the period that the operation requesting signal is continuously obtained.

13. The inhalation component generation device according to claim 1, wherein
the load is configured to generate the inhalation component from the inhalation component source, in a case that the value representing the remaining amount of the electric power source is equal to or greater than the second threshold value, and
at least one of the notification timing and the notification period of the first notification, in a case that the operation requesting signal is detected, is the same as that of the second notification.

14. The inhalation component generation device according to claim 1, wherein
the circuitry is configured to control the user interface to perform the third notification for a predetermined period that is independent of the period that the operation requesting signal is continuously Obtained.

15. The inhalation component generation device according to claim 14, wherein
the period that each of the first notification and the second notification is performed by the user interface is shorter than the predetermined period.

16. An inhalation component generation device comprising:
a load configured to vaporize or atomize an inhalation component source by electric power from an electric power source;
a user interface; and
a circuitry configured to
obtain an operation requesting signal to the load and generate an instruction for operating the load;
control the user interface to operate in one of a normal use mode; a charge requesting mode and an abnormality notifying mode; and
cause the user interface to operate in the normal use mode in a case that a value representing a remaining amount of the electric power source is equal to or greater than a first threshold value, which is a variable value, wherein
notifications of the user interface in the normal use mode, the charge requesting mode and the abnormality notifying mode are different from each other.

17. A method for controlling an inhalation component generation device comprising a load that vaporizes or atomizes an inhalation component source by electric power from an electric power source, the method comprising:
obtaining a value representing a remaining amount of the electric power source;
obtaining an operation requesting signal to the load and generating an instruction for operating the load;
performing a first notification when the value representing the remaining amount of the electric power source, that is obtained in the obtaining of the value, is equal to or greater than a first threshold value;
performing a second notification when the value representing the remaining amount of the electric power source, that is obtained in the obtaining of the value, is less than the first threshold value and equal to or greater than a second threshold value that is less than the first threshold value; and
performing a third notification when the value representing the remaining amount of the electric power source, that is obtained in the obtaining of the value, is less than the second threshold value, wherein
the first notification, the second notification and the third notification are different from each other, and
the first threshold is a variable value.

18. A method for controlling an inhalation component generation device comprising a load that vaporizes or atomizes an inhalation component source by electric power from an electric power source, a user interface and circuitry, the method comprising:
obtaining, by the circuitry, an operation requesting signal to the load and generating an instruction for operating the load;
controlling, by the circuitry, the user interface to operate in notifying one of a normal use mode, a charge requesting mode and an abnormality notifying mode,
controlling, by the circuitry, the user interface to operate in the normal use mode in a case that a value representing a remaining amount of the electric power source is equal to or greater than a first threshold value which is a variable value wherein notifications performed of the user interface in the normal use mode, the charge requesting mode and the abnormality notifying mode are different from each other.

19. A non-transitory computer-readable medium including a program, which when executed by an inhalation component generation device, causes the inhalation component generation device to perform the method according to claim 17.

* * * * *